US012745922B2

(12) United States Patent
McCawley

(10) Patent No.: US 12,745,922 B2
(45) Date of Patent: Sep. 29, 2026

(54) AEROSOL SPIROMETER AND METHOD OF USING SAME

(71) Applicant: Respiratory Management Technology, Inc., Wilmington, DE (US)

(72) Inventor: Michael McCawley, Morgantown, WV (US)

( * ) Notice: Subject to any disclaimer, the term of this patent is extended or adjusted under 35 U.S.C. 154(b) by 624 days.

(21) Appl. No.: 18/355,485

(22) Filed: Jul. 20, 2023

(65) Prior Publication Data

US 2024/0023826 A1 Jan. 25, 2024

Related U.S. Application Data

(60) Provisional application No. 63/391,731, filed on Jul. 23, 2022.

(51) Int. Cl.
*A61B 5/08* (2006.01)
*A61B 5/085* (2006.01)
(Continued)

(52) U.S. Cl.
CPC .............. *A61B 5/087* (2013.01); *A61B 5/082* (2013.01); *A61B 5/085* (2013.01); *A61B 5/091* (2013.01);
(Continued)

(58) Field of Classification Search
None
See application file for complete search history.

(56) References Cited

U.S. PATENT DOCUMENTS

| | | | | | |
|---|---|---|---|---|---|
| 7,241,269 | B2 * | 7/2007 | McCawley | ............ | A61B 5/085 600/533 |
| 7,731,666 | B2 * | 6/2010 | McCawley | ............ | A61B 5/085 600/529 |

(Continued)

OTHER PUBLICATIONS

McCawley et al. "Development of an Aerosol Dispersion Test to Detect Early Changes in Lung Function." Am. Ind. Hyg. Assoc. J. 49(7):357-366 (1988). (Year: 1988).*

(Continued)

*Primary Examiner* — Meredith Weare
(74) *Attorney, Agent, or Firm* — Thomas E. Lees, LLC

(57) ABSTRACT

An aerosol spirometer and a method of operating an aerosol spirometer. Comparison of lung function data that has been acquired by the aerosol spirometer to a known, idealized exhalation aerosol concentration profile of healthy lung operation may be used to fill in missing lung function data that arises out of resistance-based and compliance-based inhomogeneities in both aerosol penetration and aerosol deposition, where the inhomogeneities may be mathematically correlated to time constant data that in turn may be directly correlated to ventilation. This data, when added to the idealized exhalation aerosol concentration profile, produces a more complete data-informed exhalation aerosol concentration profile from which an inference may be made about possible lung dysfunction of an individual using the aerosol spirometer. A machine learning model may be trained on the lung function data that has been collected by the aerosol spirometer such that upon use, the machine learning model may provide a predictive inference related to either an onset or worsening of the lung dysfunction.

20 Claims, 12 Drawing Sheets

(51) Int. Cl.

| | |
|---|---|
| ***A61B 5/087*** | (2006.01) |
| ***A61B 5/091*** | (2006.01) |
| ***A61M 11/00*** | (2006.01) |
| ***A61M 11/04*** | (2006.01) |
| ***A61M 15/00*** | (2006.01) |
| ***A61M 16/20*** | (2006.01) |

(52) U.S. Cl.

CPC ........... *A61M 11/001* (2014.02); *A61M 11/04* (2013.01); *A61M 15/0021* (2014.02); *A61M 16/208* (2013.01); *A61M 2205/50* (2013.01)

(56) References Cited

U.S. PATENT DOCUMENTS

| | | | | |
|---|---|---|---|---|
| 7,988,641 | B2 * | 8/2011 | McCawley .......... | A61B 5/0813 600/529 |
| 8,353,845 | B2 * | 1/2013 | McCawley .......... | A61B 5/0813 600/300 |
| 2005/0045175 | A1 * | 3/2005 | McCawley .......... | A61B 5/0813 128/200.14 |
| 2005/0066968 | A1 * | 3/2005 | Shofner ................. | A61B 5/411 128/204.18 |
| 2008/0015456 | A1 * | 1/2008 | McCawley .......... | A61B 5/0813 600/529 |
| 2010/0222692 | A1 * | 9/2010 | McCawley ............ | A61B 5/085 600/532 |
| 2011/0247611 | A1 * | 10/2011 | McCawley .......... | A61B 5/0813 128/200.14 |
| 2015/0297118 | A1 * | 10/2015 | Löndahl ................. | A61B 5/082 600/532 |
| 2018/0296124 | A1 * | 10/2018 | Karakaya ............. | A61B 5/7278 |

OTHER PUBLICATIONS

Brown et al. “Dispersion of Aerosol Boluses in the Human Lung: Dependence on Lung Volume, Bolus Volume, and Gender.” J Appl Physiol (1985). Nov. 1995;79(5):1787-95. (Year: 1995).*

Kohlhäufl et al. “Diagnosis of Emphysema in Patients with Chronic Bronchitis: A New Approach.” Eur Respir J. Oct. 1998;12(4):793-8. (Year: 1998).*

McCawley et al. “Comparison of the Measurement of Obstructive Pulmonary Disease Using Spirometry, Plethysmography and Aerosol Dispersion Techniques.” EC Pulmonology and Respiratory Medicine 8.2 (2019): 102-111. (Year: 2019).*

* cited by examiner

AEROSOL SPIROMETER AND METHOD OF USING SAME

This application claims the benefit of U.S. Provisional Patent Application Ser. No. 63/391,732 that was filed on Jul. 23, 2022.

TECHNICAL FIELD

The present disclosure relates generally to an aerosol dispersion device and method to detect early changes in lung function, and more particularly to using the aerosol dispersion device such that aerosol particles that are introduced to the lungs during a test under normal breathing conditions are used to adjust time constants by taking into consideration both penetration and deposition inhomogeneity in order to directly measure lung ventilation and from that predict a corresponding indicia of lung dysfunction.

BACKGROUND

Lung abnormalities can significantly impact a person's ability to breathe, and in some cases may lead to other morbidities, including death. Among the various ways to determine the health of the respiratory system, measuring ventilation—the ability to move fresh, oxygen-rich air into the lung, mix it with the air already in the lung while removing the carbon dioxide-laden air out of the lung—may be used to provide indicia of certain abnormalities, including asthma, bronchitis, cystic fibrosis, chronic obstructive pulmonary disease (COPD), emphysema and pneumonia, among others. Traditional forms of testing for ventilation as a measure of pulmonary function as a way to detect the presence of these and other adverse medical conditions may include those based on flow volume spirometry, gas diffusion, body plethysmography or change-based or stress-based breathing protocols. All of these exhibit various shortcomings.

SUMMARY

The author of the present disclosure has discovered that using an aerosol-based spirometric approach as a direct measure of ventilation in conjunction with a data-informed mathematical (algorithmic) model is a better predictor of certain measures of lung function. In such an approach, the ventilation that takes place within the respiratory tract may be directly modeled as a mechanical system rather than a chemical one. In particular, the timed introduction of aerosol particles into the respiratory tract from the aerosol spirometer may be used to measure how long it takes for air to travel into and out of the lungs. Two particular parameters-airway resistance and airway compliance—are measures of differences between inhalation and exhalation of the various pathways in the lung that in turn cause aerosol dispersion. This dispersion is used to determine time constants that in turn provides travel time, as well as provide a measure of aerosol sequencing and distribution within each of the numerous individual airways. Such time constants for each of the airways, along with known aerosol volume, are used as a way to directly quantify ventilation. Moreover, by applying these parameters to a statistical model (such as a gamma distribution function) to correct for penetration and deposition data non-homogeneities allows precise aerosol location determinations and consequent mapping of the lung. This in turn can be correlated to certain lung anomalies, as well as provide a more detailed, targeted location for the placement of medicaments.

The author of the present disclosure has additionally recognized that by using short pulses of aerosol that are introduced into a normal breathing cycle, time constants can be measured that in turn can be corelated to indicia of obstruction or restriction from which lung function dysfunction may be inferred. Within the present disclosure, nearly equivalent time constants for each of the lung pathways are indicative of homogeneous ventilation and healthy lung function whereas larger and uneven time constants for such pathways are indicative of inhomogeneities in the ventilation and lung dysfunction arising out of such obstructions or restrictions. Significantly, the device and method is not merely capable of identifying whether an obstruction or restriction is present, but also their location within the lung.

The author of the present disclosure has further recognized that while acquired aerosol bolus data losses due to physiological non-homogeneities such as lung dead space, "first-in/last-out" and others that otherwise would adversely impact the accuracy of a statistical model that is used to calculate ventilation values will improve the ventilation calculation accuracy, such knowledge and its use in correcting the model is not sufficient in and of itself. The author of the present disclosure additionally recognized that using the statistical model in conjunction with a trained machine learning (ML) model to take into consideration both penetration and deposition non-homogeneities can provide a more thorough understanding of sparse, missing data in an exhaled aerosol bolus than merely considering penetration-based corrections to such data and by controlling the breathing rate of the subject such that deposition of the aerosol in the lung does not occur. In particular, such an enhanced understanding may be used to further adjust the time constants by taking into consideration not just the deposition and penetration-related differences in aerosol particle concentration, but also how such differences can be used to pinpoint locations of certain inhomogeneities that in turn can be correlated through such ML to provide predictive analytics for the diagnosis and possible treatment of a particular adverse breathing condition within the respiratory tract.

According to an aspect of the present disclosure, a method of performing an aerosol dispersion-based respiratory system test is disclosed. The method includes configuring an aerosol spirometer to introduce an aerosol into the respiratory system such that upon receipt within the aerosol spirometer of an inhalation portion of a normal breathing cycle from a patient, an aerosol pulse is provided such that the aerosol pulse mixes with ambient air from the inhalation portion, after which the aerosol spirometer detects both numerous aerosol particles contained within the inhalation portion and numerous aerosol particles contained within an exhalation portion. Losses within the exhalation portion may be accounted for through at least one of reducing one or more of impaction and sedimentation through control of a breathing pattern of the patient and creating a data-informed exhalation aerosol concentration profile the latter of which is done by comparing a distribution of the detected aerosol particles contained within the exhalation portion to an idealized exhalation aerosol concentration profile, and then populating the idealized exhalation aerosol concentration profile with at least a portion of additional detected aerosol particles contained within the normal breathing cycle to generate an updated exhalation aerosol concentration profile. From this, aerosol dispersion transit times are calculated and then, based on the calculated aerosol dispersion transit times, a concentration distribution of the detected aerosol particles contained within the normal breathing cycle is determined, wherein at least a portion of the calculation is based on the reduced losses. A signal that corresponds to the concentration distribution is then transmitted to a processor-based controller so that a determination of whether the respiratory system is suffering from an adverse lung condition may be made, based on a correlation between symptoms indicative of a lung function to the transmitted concentration distribution.

According to another aspect of the present disclosure, an ML-based system for analyzing lung function is disclosed. The ML system includes an aerosol spirometer and a computer with at least one processor and a non-transitory computer readable medium storing machine-readable instructions. Upon operation, the ML system receives numerous data points from the aerosol spirometer (where the plurality of data points corresponds to aerosol particles that have been introduced by the aerosol spirometer into the lung of an individual for traversal therethrough and subsequently detected) and determines a time-based indication of one or more of aerosol deposition and aerosol penetration within the lung. The time-based indication corrects for losses within an exhalation portion of a normal breathing cycle through a data-informed exhalation aerosol concentration profile that is based on a comparison of a distribution of the various data points to an idealized exhalation aerosol concentration profile. In this way, the idealized exhalation aerosol concentration profile becomes populated with at least a portion of additional data points from which an updated exhalation aerosol concentration profile is created. The ML system further predicts a lung condition based on a correlation between various symptoms indicative of a lung function and the updated exhalation aerosol concentration profile. In addition, the ML system may transmit the predicted lung condition to a user.

According to another aspect of the present disclosure, a method of performing an aerosol dispersion-based respiratory system test on a patient is disclosed. The method includes configuring an aerosol spirometer to introduce an aerosol into the respiratory system. In this way, upon receipt within the aerosol spirometer of an inhalation portion of a normal breathing cycle from the patient, an aerosol pulse is provided such that it mixes with ambient air from an inhalation portion of the normal breathing cycle. Numerous aerosol particles contained within the inhalation portion are then detected with the aerosol spirometer, as are numerous aerosol particles contained within an exhalation portion of the normal breathing cycle. In addition, a machine learning model is used to calculate aerosol dispersion transit times of the detected aerosol particles, wherein data points representative of the aerosol dispersion transit times are corrected for losses within the exhalation portion through a data-informed exhalation aerosol concentration profile that is based on a comparison of a distribution of the data points to an idealized exhalation aerosol concentration profile. In this way, the idealized exhalation aerosol concentration profile becomes populated with at least a portion of additional data points such that an updated exhalation aerosol concentration profile is created. In addition, a concentration distribution based on the updated exhalation aerosol concentration profile is determined so that a signal that corresponds to the concentration distribution is transmitted to a processor-based controller after which it may be determined that the respiratory system is suffering from an adverse lung condition based on a correlation between various symptoms indicative of a lung function and the concentration distribution.

BRIEF DESCRIPTION OF THE DRAWINGS

The embodiments set forth in the drawings are illustrative in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

A technical problem relates to how to accurately quantify when a patient may be experiencing the onset of an adverse breathing condition through data acquired by ventilation testing. More specifically, this technical problem particularly extends to achieving such accuracy when data being acquired through such testing is sparse. In this regard, aspects of the present disclosure provide a technical solution that compensates for sparse data sets by first using a portable inhalation testing device and method that promotes more thorough inhalant placement within the respiratory tract and second algorithmically corrects for sparsity within the acquired data such that predictive analytics based on the algorithmic correction may be used to diagnose—and optionally provide clinical decision support for treatment—of one or more adverse respiratory tract conditions. This technical solution manifests itself as a positive technical effect by reducing or eliminating testing inaccuracies while simultaneously providing real-time or near real-time analysis of a respiratory tract condition along with reducing the weight and complexity of the testing device.

Figure 1:
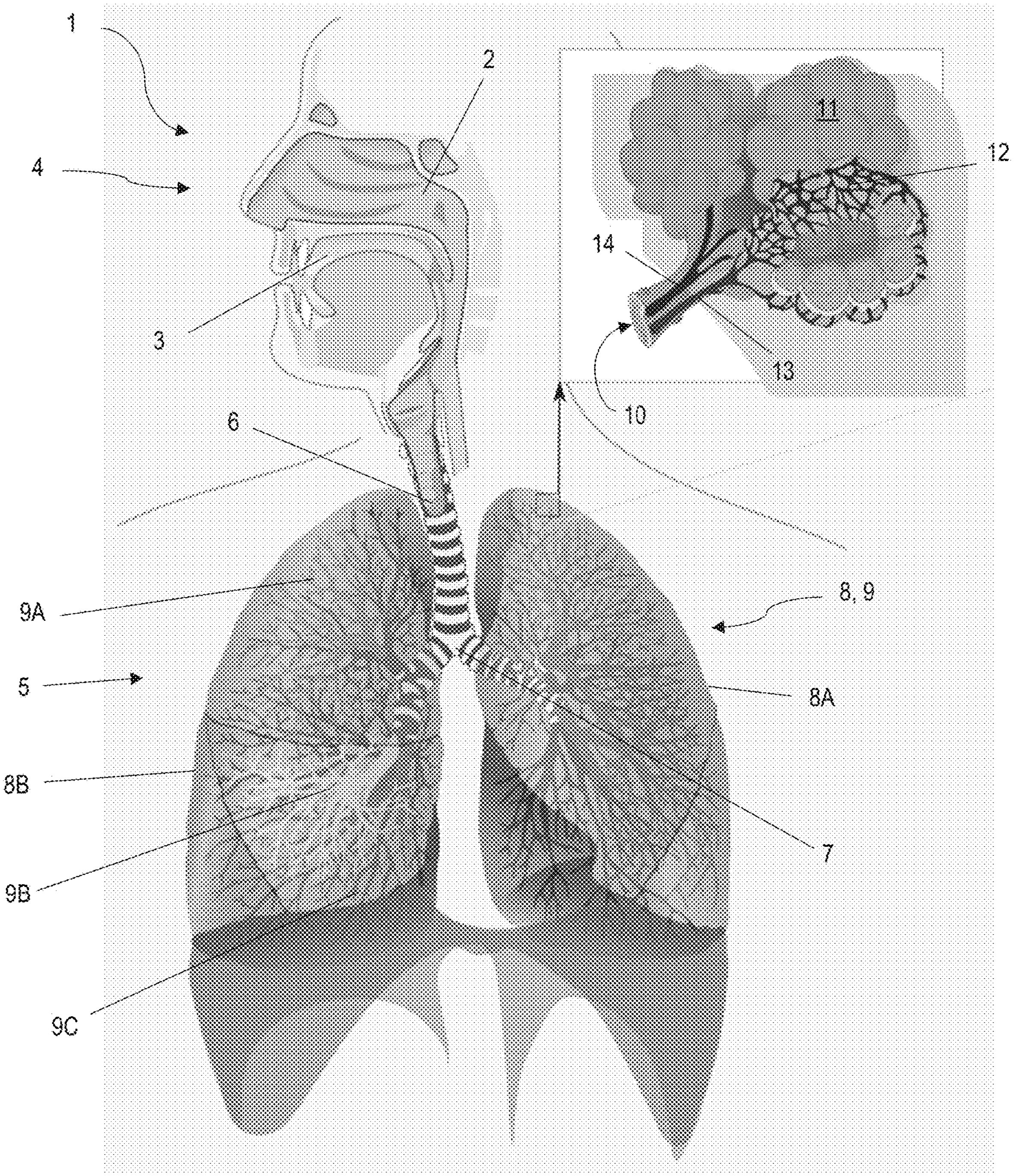
FIG. 1 depicts a simplified view of a notional human respiratory system.

Referring first to FIG. 1, a notional human respiratory system 1 is shown. In the respiratory cycle of a normal breathing pattern, air introduced by an inhalation step enters into one or both of a nasal cavity 2 or oral cavity 3 of an upper respiratory tract 4 and then passes into a lower respiratory tract 5 through a trachea 6 and bronchial tree 7 to each of a pair of lungs 8 (represented as right and left lungs 8A, 8B). This air travels into various lobes 9 (superior 9A, middle 9B and inferior 9C) through pathways that define ducts 10 that terminate in a cluster-like alveolar sac 11 that is made up of numerous individual alveoli. A capillary network 12 is situated on a membranous outer surface of each of the alveoli and is connected to pulmonary arteries 13 and veins 14 for the exchange within the blood stream (not shown) of the incoming air with carbon dioxide that has been produced by the body during normal pulmonary functions. Thus, as atmospheric air is introduced through bronchioles into the internal volume of each of the various alveolar sacs 11, it interacts with the blood that is flowing through the vessels that make up the capillary network 12 such that (among other processes) a perfusion-based convective transport takes place at the membranes. Such transport involves conveying the fresh oxygen contained within the air to the blood flowing through the pulmonary arteries 13 while the carbon dioxide that has built up in the muscles is conveyed by the blood that flows through the pulmonary veins 14 to the air that is contained within the internal volume. In this way, the air being exhaled—as a measure of ventilation—contains a mixture of unreacted oxygen and carbon dioxide. This mixture leaves the respiratory system 1 through a substantially reverse path to that of the inhalation step where such path is made up of the ducts 10, lobes 9, lungs 8, bronchial tree 7, trachea 6 and one or both of the nasal cavity 2 and (optionally) the oral cavity 3. In this way, the lungs 8 function as a mechanical mixing tank where the inhaled, oxygen-rich air of the atmosphere is combined with the oxygen-depleted air of the alveolar sacs 11. By mixing these two sources of air together, the ventilation process provides oxygen to the blood in the capillary network 12 that surrounds the alveolar sacs 11.

Interference with this normal gas exchange (and therefore, ventilation) takes place in people who have asthma, bronchitis, cystic fibrosis, COPD, emphysema or related maladies. This interference may be quantified by physiological modeling techniques that rely upon a pair of parameters, namely resistance and compliance. In the former, features such as respiratory path length, cross-section and surface texture are often determining factors, while in the latter a change in lung volume relative to pressures under static conditions provides indicia of the ability of the lungs 8 to resist recoil upon removal of the pressurized air source. An electrical analog to the resistance to air flow within the lungs 8 resembles the resistance to current flow within an electrical circuit, while an electrical analog to the elastically compliant ability of the lungs 8 to expand and contract resembles the energy storage that takes place in a capacitor. A multiplicative product of resistance and compliance results in a time constant that can be correlated to the ventilation taking place within the lungs 8, where relatively large time constants are correlated to imbalances in otherwise normal (that is to say, homogeneous) ventilation that in turn are indicative of lung blockage (such as in the form of an obstruction) or fibrosis (such as in the form of a restriction) relative to relatively small time constants. The author of the present disclosure has discovered that the convective transport that takes place within the membranous capillary network 12 is such that inaccuracies in time constant calculation may arise through the use of conventional approaches, especially those that rely on approaches that predominantly or solely measure flow volumes. Significantly, the precise value of the time constant for any given airway is not as important as the total distribution (the mean and standard deviation) of time constants for all of the airways involved. In particular, the distribution should be identical for all healthy individuals, making it predictable for all healthy subjects, regardless of their age, height, weight, gender, breathing rate (so long as the breathing rate does not cause particle deposition losses as discussed elsewhere in the present disclosure) or breathing depth. This in turn improves stable predictability of pulmonary function by removing the need to make corrections for any measure of the homogeneity of ventilation of the lungs. The author of the present disclosure has further discovered that because of the stable, repeatable nature of the aerosol spirometry approach, any given breathing measurement may be replicated and averaged over multiple breaths in a manner not possible with certain traditional approaches (such as flow volume spirometry); in this way, such signal averaging enhances the precision and sensitivity of the test procedure.

Figure 2A:
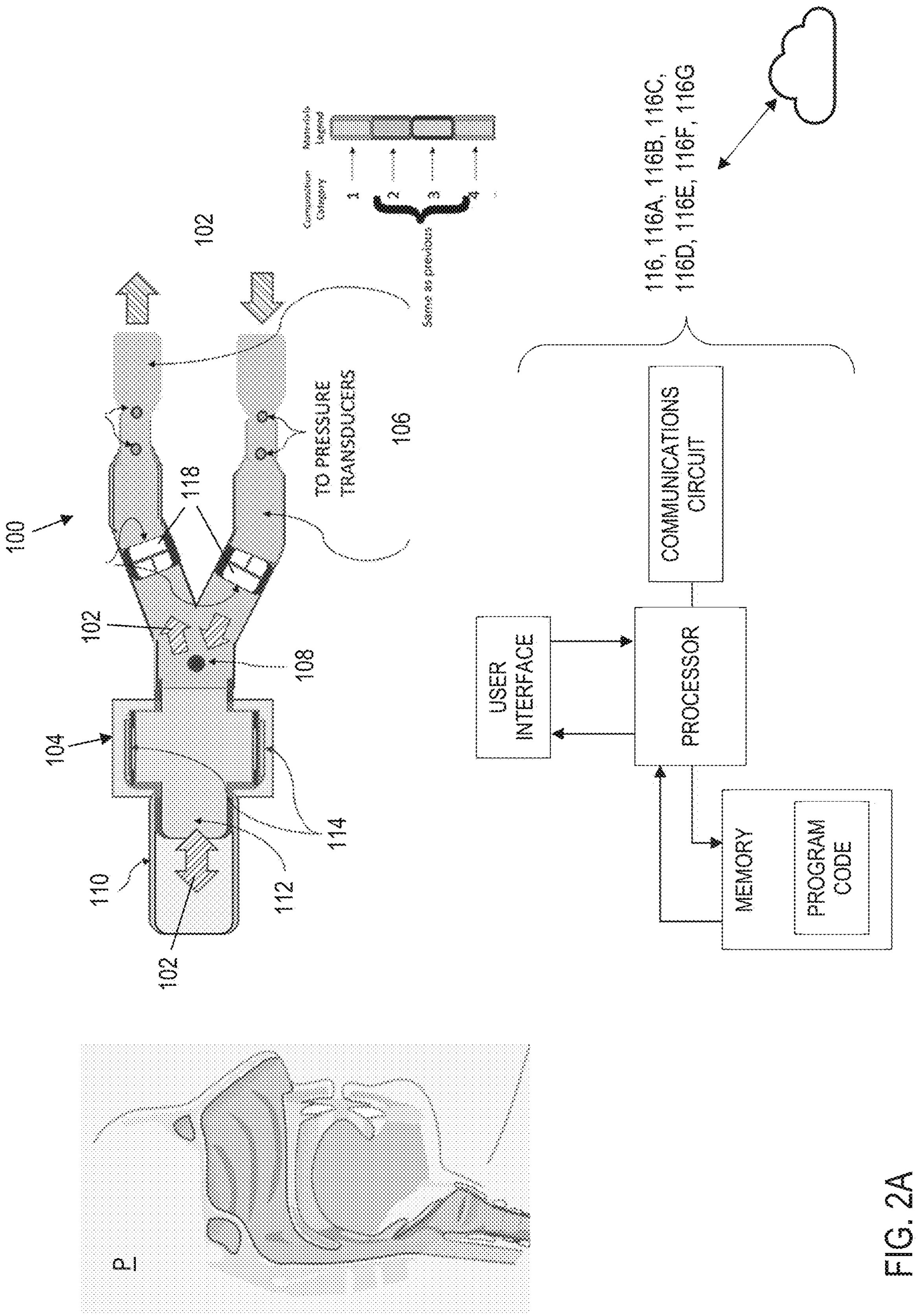
FIG. 2A depicts a top view of a stylized aerosol spirometer that may be used to determine the lung function of the respiratory system of FIG. 1.
Figure 2B:
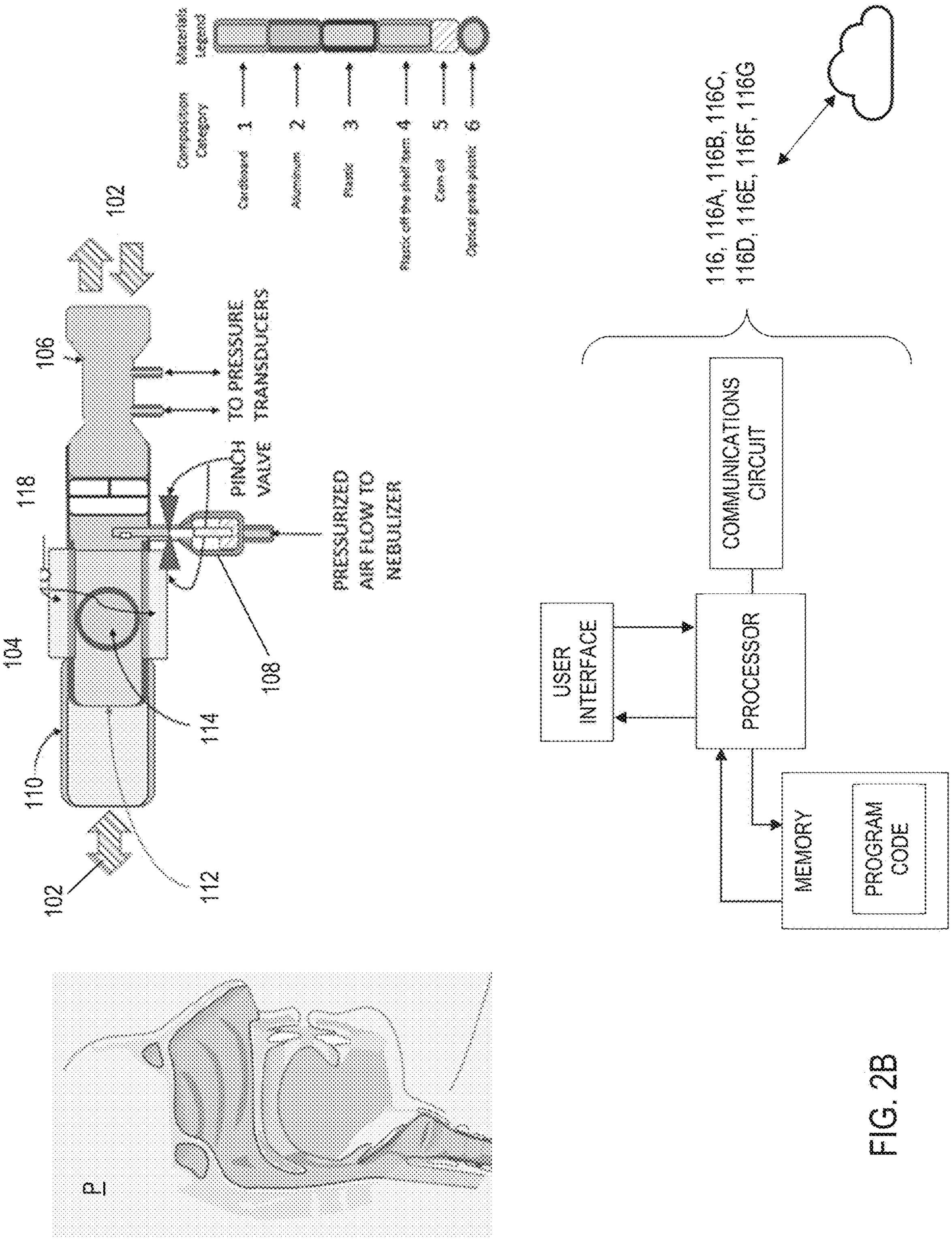
FIG. 2B depicts a side view of the aerosol spirometer of FIG. 2A.
Figure 2C:
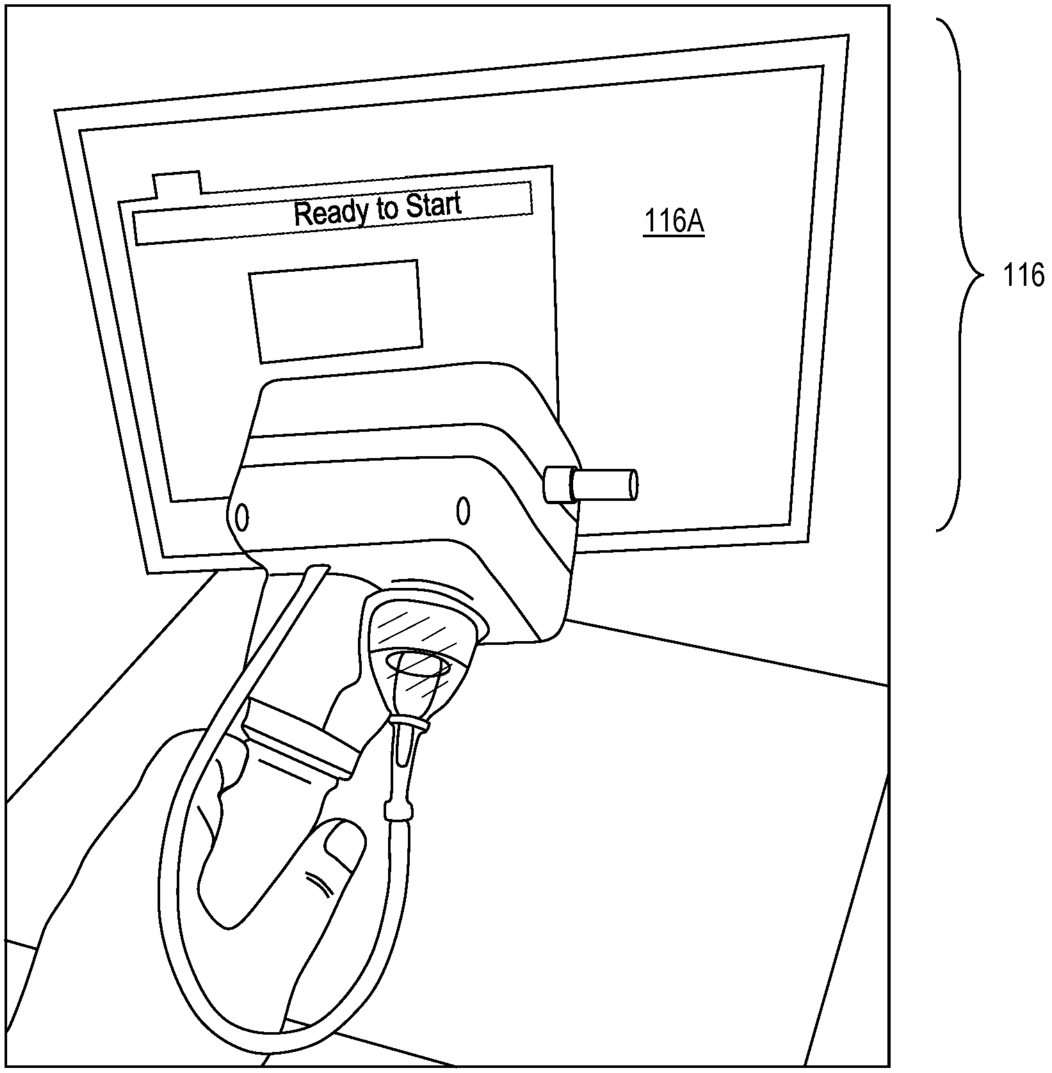
FIG. 2C depicts the aerosol spirometer in use with a controller.
Figure 3A:
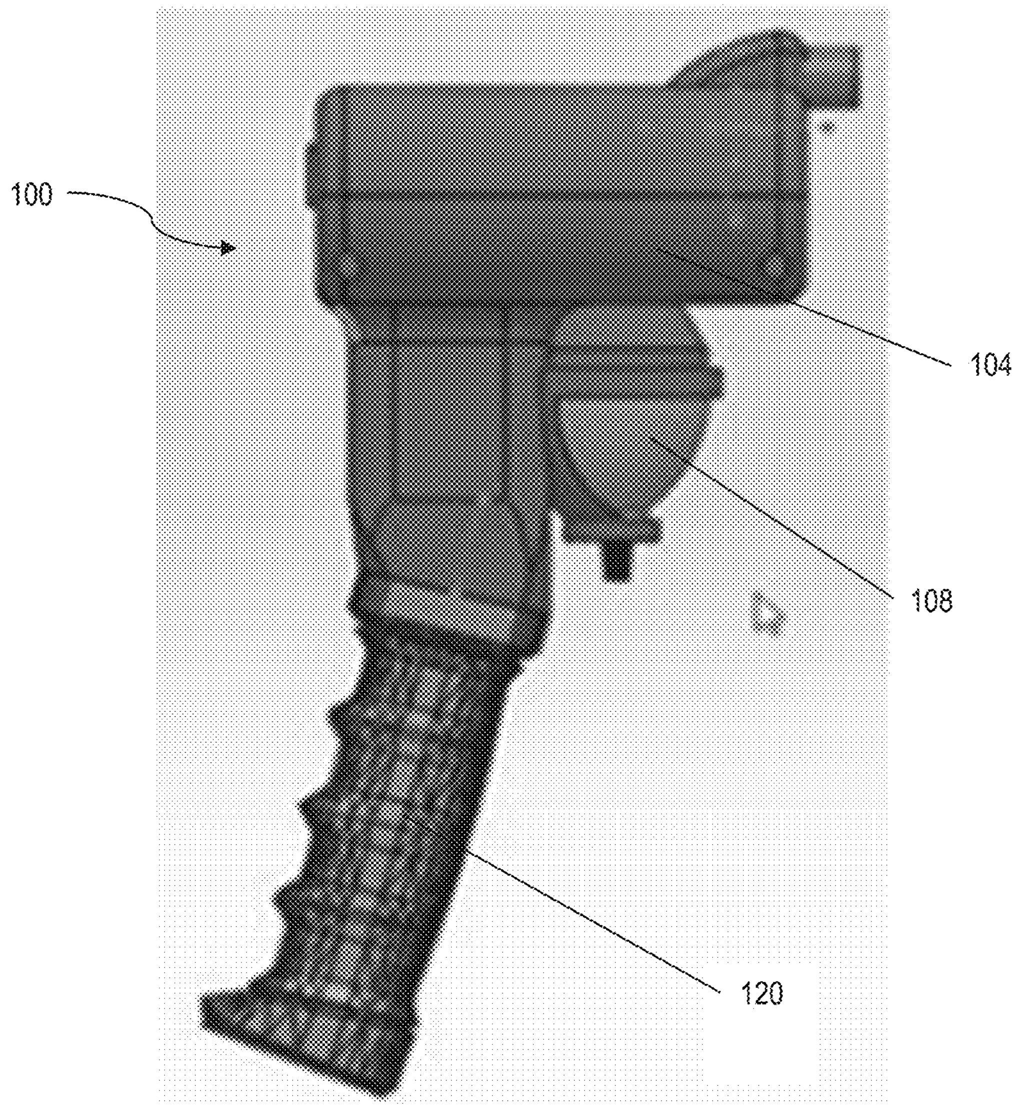
FIG. 3A depicts a left side elevation view of one portable embodiment of the aerosol spirometer that may be used to determine the lung function of the respiratory system of FIG. 1.
Figure 3B:
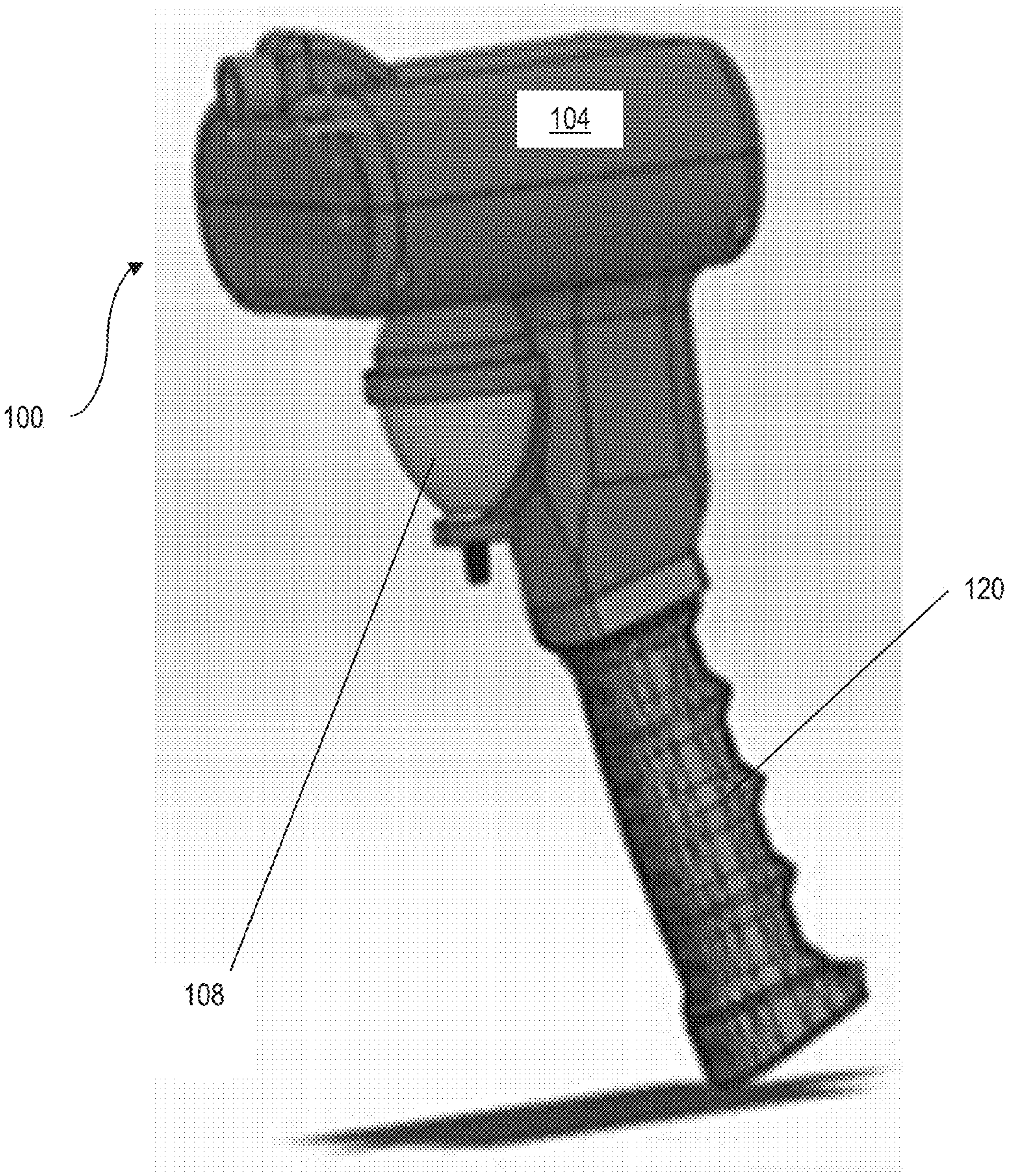
FIG. 3B depicts a right front view of the aerosol spirometer of FIG. 3A.
Figure 3C:
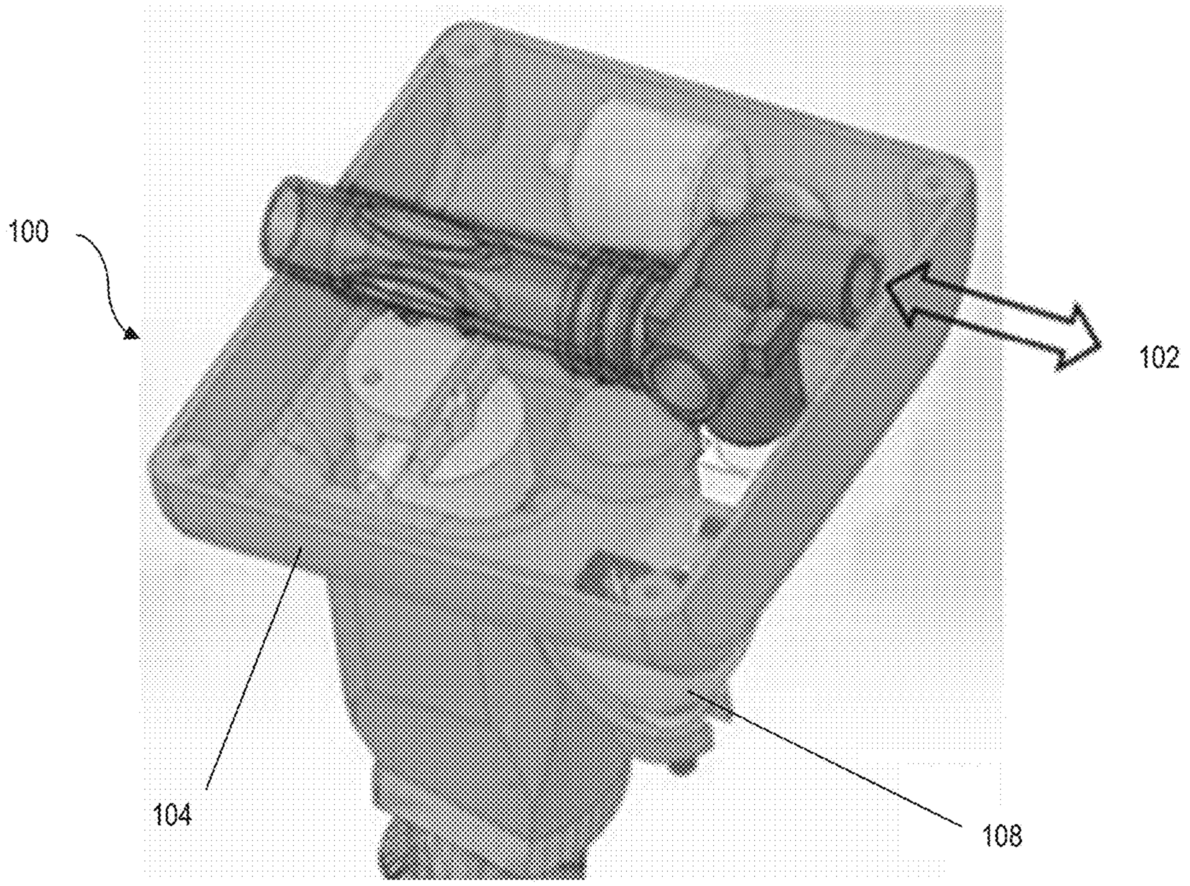
FIG. 3C depicts a perspective internal view of a portion of the aerosol spirometer.
Figure 3D:
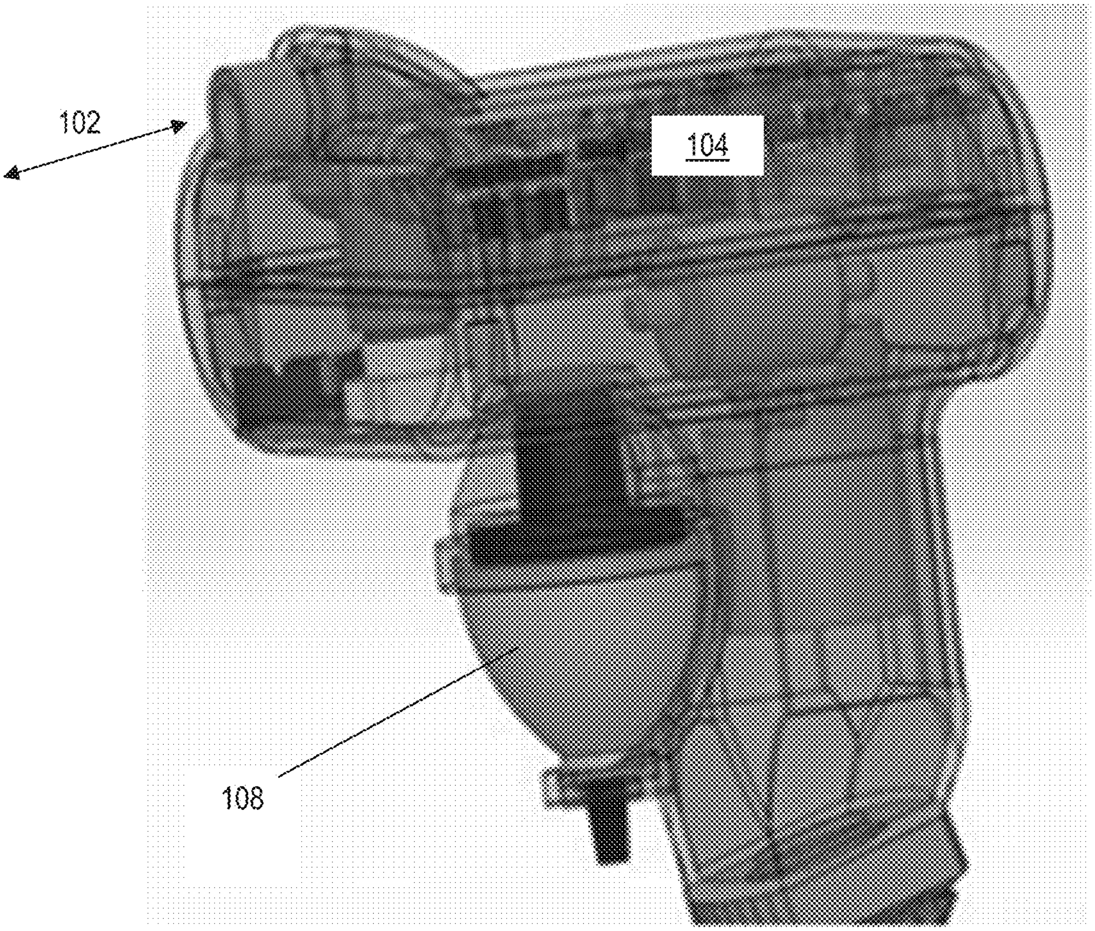
FIG. 3D depicts a partial see-through right front view of the aerosol spirometer.

Referring next to FIGS. 2A through 2C, top (FIG. 2A) and side (FIG. 2B) views respectively of an aerosol spirometer (also referred to as an aerosol dispersion device) 100 are shown. A breathing flowpath 102 is formed within a structural housing 104 to extend between a patient P at a proximal end to one or more pneumotachometers 106 at a distal end, while an aerosol dispersion mechanism 108 may be secured to the housing 104 or otherwise be cooperative therewith in order to introduce an aerosol A in order to place it in fluid communication with the breathing flowpath 102. A mouthpiece 110 is sized and shaped to be placed over a complementary-sized and shaped proximal portion of the housing 104 that defines an interior sensor chamber 112 therein. In one form, the mouthpiece 110 is made to be interchangeable and disposable, and as such may be made from inexpensive materials such as cardboard or a biocompatible plastic, while the housing 104 may be made from a suitable biocompatible structural material, such as stainless steel. Proceeding distally along the flowpath 102 in a direction away from the patient P, the shape and volume of the sensor chamber 112 enlarges to define a pair of sensor windows 114. This portion of the sensor chamber 112 and sensor windows (typically in the form of a photocell or photometer) 114 are configured to measure an airflow along the breathing flowpath 102 as well as to detect the passage of aerosol A particles that have been introduced therein from the aerosol dispersion mechanism 108 as the patient P inhales and exhales.

In one form, the aerosol dispersion mechanism 108 may be a nebulizer that contains a volume of medicament, tracer or other material capable of being placed into aerosol A form such that upon introduction of pressurized air from a source (for example, a compressor and an oxygen tank, not shown), the pressurized air interacts with the material that in turn passes through conduit that is fluidly coupled to the aerosol dispersion mechanism 108 on its way to the portion of the breathing flowpath 102 that extends through the housing 104. In one form, the valves 118 are one-way valves, such as a check valve. In another form, a pressure regulator (not shown) may, upon instructions from a controller 116, selectively open and close valves 118 that are situated in each of the branches (specifically, an inhalation branch and an exhalation branch shown at the bottom and top respectively of the flowpath 102 depicted in FIG. 2A) of the portion of the flowpath 102 that is fluidly distal of the aerosol dispersion mechanism 108.

It is beneficial to understand and control the size of the medicament, tracer or other aerosol A droplets or particles that are introduced from the aerosol dispersion mechanism 108. In particular, these sizes are important for knowing certain gravitational-based sedimentation compaction or other measures of aerosol A travels, settling or the like. The author of the present disclosure has determined that aerosol A larger than about 2 μm to about 5 μm diameter will achieve higher degrees of impaction than those of smaller diameter. Likewise, smaller aerosols A (for example between about 0.5 μm and 0.7 μm) may be small enough to minimize sedimentation or impaction, but more easily passed through the respiratory system 1 for minimal loss due to contact with the tissue in the lungs 8 that in turn may facilitate the delivery of medicaments or the like to a larger portion of the lungs 8. Likewise, even smaller aerosols A (for example, those less than about 1.0 μm) may be beneficial in circumstances where sedimentation-based aerosol activity is desired.

In one form, the author of the present disclosure has found that while impaction may be used for the delivery of certain medicaments, others (for example, those less than 1 μm, less than 0.7 μm, less than 0.5 μm) may be more useful in generating time constants and other measures of lung functions as disclosed herein.

As will be discussed in more detail as follows, the concentration of individual particles that make up the aerosol A may be measured, and from this, the time constants derived. These in turn may be compared to known baselines that can be analyzed either directly (such as by a physician, based on his or her experience and knowledge) or by an algorithmic clinical decision support (CDS) mechanism the latter of which may implement the ML models that will be disclosed in more detail in conjunction with FIG. 6. It will be appreciated that restorative corrections may need to be made to account for certain portions of the exhalation portion of a normal breathing cycle. Within the present disclosure, options exist for making such restorative corrections that may otherwise manifest themselves as a loss of a generated and transmitted signal, such as that due to low aerosol concentration. In one form, the patient P may be made to breathe faster in order to reduce residence time of the aerosol in the lungs 8, 9 for sedimentation. In another form, it is possible that an increased breathing flow rate may result in loss due to increased impaction rates that has the effect of nullifying the gains from losses due to sedimentation. In at least this latter form, the ML model can then apply a particle loss algorithm (as part of the CDS mechanism) to the initial portion of an exhaled particle concentration profile as a way to restore the signal through the creation of an updated exhalation aerosol concentration profile.

Significantly, the configuration of the aerosol spirometer 100 in general and the check valve nature of the valves 118 is such that restricted flows being forced on the inhaled and exhaled air which is integral to allowing a person to breathe while avoiding cross contamination of the flows. In particular, it is recognized that the ports to the one or more pneumotachometers 106 could trap mucus droplets and microbes that may be suspended in the breathing flows. By having an inward facing valve 118 on the inhalation branch of flowpath 102, none of the exhaled sputum is permitted to pass through that branch, while on the exhalation branch the exhaled sputum could travel through its valve 118 and branch while prohibiting inhaled air from passing. In one form, the valves 118 are made to be disposable so that even if they become contaminated with sputum, they can readily be taken out and discarded. In a similar way, other portions of the aerosol spirometer 100 (such as the mouthpiece 110, as previously noted) may be made replaceable or interchangeable. In one form, the mouthpiece 110 may be electronically tagged (such as through a pre-coded electronic tag). In that way, the aerosol spirometer 100 may be disabled if it is not in its proper use place. Such interlocking control provides additional security that has the effect of guarding against anyone using anything other than the FDA-approved material and nebulizer, such as those that are packaged as kits that may also include the mouthpiece 110 from an authorized manufacturer and FDA-approved manufacturing facility.

Referring with particularity to FIG. 2C, the controller 116 may be resident in any computing environment (whether stand-alone or networked) and be defined by various configurations or architectures, including mobile devices personal computers, multi-processor systems, network PCs, minicomputers, mainframe computers or the like. As can be seen, controller 116 may include various components such as a user interface 116A, processor 116B, memory 116C that may contain data structures, program code, machine codes, native instruction sets, computer readable instructions 116D or the like such that upon loading into memory 116C, the program code 116D may execute one or more steps in a manner consistent with the methods disclosed herein. In addition, controller 116 may include a communications circuit 116E that may be either wired or wireless such in when configured as the latter, it may include a suitable radio-frequency transceiver 116F that can access an external network (not shown), including such networks with distributed computational functionality, whether in the cloud 116G or as part of a local are network (LAN), virtual private network (VPN) or the like.

The user interface 116A will be understood to include any suitable piece of software, hardware or combination thereof to provide for interactions between an operator and the aerosol spirometer 100 or other machine cooperative therewith. In one form, the user interface 116A is configured as a graphical user interface for one or both of receiving as input a command from an operator and providing feedback thereto. The processor 116B will be understood to include any and all logic devices that may perform at least arithmetic and logic functions on data contained within the memory 116C, as well as on input data such as that which is received through the user interface 116A.

In one form, the processor 116B is configured as a central processing unit (CPU), application-specific integrated circuit (ASIC), field-programmable gate array (FPGA), graphical processor unit (GPU), tensor processing unit (TPU) or the like. Likewise, the processor 116B may be an aggregation of numerous discrete, dedicated chips in a distributed architecture, or be include varying degrees of component integration, including that with memory 116C in order to mimic a system-on-a-chip (SoC) architecture. Depending on the configuration, various ML models such as those discussed in conjunction with FIG. 6 may be executed, including those where memory 116C may store a trainable ML algorithm that can be accessed and executed by the processor 116B in order perform a classification, regression or clustering-based model or analysis, as well as to update the state of the ML algorithm through corresponding updates to the memory 116C. In a particular form, the memory 116C may be configured to store in-memory analytics such that the ML algorithms and related models can be made to run in order to provide direct memory 116C access of the analytics, thereby providing the ability to perform more real-time calculations on the acquired data such as temperature data, pressure data, photocell data, flowrate data, time-of-flight data or the like, including those from other sensors that may be signally cooperative with the aerosol spirometer 100. Likewise, the data being evaluated by the in-memory analytics can be spread across numerous parallel or distributed computing processors 116B as a way to divide larger amounts of data processing to further promote real-time activities. In situations where the calculations being performed involve large-scale matrix multiplication, such as those associated with deep learning neural networks or other ML approaches where large amounts of parallel data may need to be processed, the processor 116B may be configured as the aforementioned GPU, TPU, ASIC or other specialized logic device.

The program code 116D will be understood to include the organized collection of instructions and computer data that make up particular application software and system software the latter of which may include operating system software and basic input/output that relates to the operation of the computer itself. In one form, the application software cooperates with the user interface 116A between a user and the system software, while the system software acts as an interface between the application software and the various hardware components within the controller 116. In one form, both the system software and the application software may be stored on memory 116C. Taken in their totality, such software provides programmed instructions that may be implemented on the processor 116B to allow it to interact with the aerosol spirometer 100 or other computer-based equipment in order to perform one or more of the data acquisition, processing, communicating, analysis and related functions—as well as device control—disclosed herein. For example, source code created by a programmer may be converted into executable form as machine code for use by the processor 116B; such machine code is predefined to perform a specific task in that they are taken from a machine language instruction set known as the native instruction set that may be part of a shared library or related non-volatile memory that is specific to the implementation of the processor 116B and its particular Instruction Set Architecture (ISA). In this way, the ISA provides a conceptual model that describes the specific implementation of processor 116B in such a way to correlate various programming functional operations. Among other things, the ISA is responsible for organization of memory and registers, data structures and types, what operations are to be specified, modes of addressing instructions and data items, as well as instruction encoding and formatting. Thus, the ISA acts as an interface between the hardware of the processor 116B and the system or application software through the implementation of the machine code all of which are predefined within the ISA. As such, the machine code imparts structure to the architecture of a particular processor 116B. Specifically, the machine code is in the form of a program structure that may be made up of a set of individual codes that together may be depicted herein as a flow diagram or related sequence that operates on the data structure that itself may be in one form an organized list, array, tree or graph of the collected data from the aerosol spirometer 100. As such, a structural relationship exists between the processor 116B, the memory 116C and the machine code regardless of whether additional computational activities (such as those associated with the ML algorithms and models that are discussed elsewhere in this disclosure) are or are not being used. As such, software instructions such as those embodied in the corresponding portion of the machine code configure the processor 116B to provide the functionality as discussed herein.

With this understanding, the machine code taken from the native instruction set in turn is arranged as a specific structural conduit to allow the processor 116B and memory 116C to communicate with particular system or application software. Accordingly, the predefined structure embodied in the machine code allows them to become a part of the processor 116B in a necessary way such that together they can implement unique operations in response to the particular commands from the program structure. In this way, various operations—which may include data handling operations, arithmetic operations, control flow operations, addressing operations, logic operations and memory location operations—may be performed that are unique to the aerosol spirometer 100. For example, the machine code may be made to reside on memory 116C to facilitate cooperation with the processor 116B in a machine-specific manner. In one form, this allows the implementation of an ML classification model (such as that which is trained as a neural network, decision tree, Bayesian network or other approach as discussed elsewhere in this disclosure) to automatically perform predictions of potentially adverse lung conditions for a person from whom one or more forms of the acquired data are received by the aerosol spirometer 100. Likewise, the data that is being input to, manipulated by or output from the aerosol spirometer 100, as well as any data that is operated upon by such an ML classification model, may be stored in memory 116C as data structures or related contents in the form of arrays (including vectors as their one-dimensional tensor variant, matrices as their two-dimensional tensor variant and tabbed matrices as three-dimensional and subsequent n-dimensional variants such as so-called notebook tabs), link lists, stacks, queues, tree structures, graphs, or the like. In this way, these multidimensional arrays differ from tensors in that while they are both types of objects, the tensor is a type of function with an array of numbers arranged on a regular grid with a variable number of axes while the multidimensional array forms a data structure that may be used to represent the tensor in a coordinate system, thereby giving it unique higher dimensional attributes.

The communications circuit 116E will be understood to include all hardware, software and firmware needed to provide connectivity to outside computer or related communications-based resources, such as for allowing the exchange of data and corresponding analysis, instructions, alerts, reports or the like to a remote client, database or related computational facility. Regardless of whether the signals are being conveyed in a wired or wireless format, it will be understood that the communications circuit 116E contains all of the functionality necessary within its respective protocol stack, including for all known network architectures. For example, the suitable radio-frequency transceiver 116F may be used in conjunction with a wireless external network such as that associated with LANs, VPNs, Metropolitan Area Networks (MANs), Wide Area Networks (WANs) or the like. Furthermore, even in situations where at least a portion of the network has wireless capability, it will be appreciated that it still may cooperate with a wired network, such as the internet as a way to have certain analytics and related calculations performed, including those taking place in the cloud 116G.

Referring next to FIGS. 3A through 3D, various views of the aerosol spirometer 100 that highlight its portable nature according to an aspect of the present disclosure are shown.

In the non-limiting embodiment shown, the aerosol spirometer 100 defines a handheld form factor through handle 120. As such, the overall package is approximately the size, cost and weight of a continuous positive airway pressure (CPAP) apparatus. The pneumotachometers 106 that are shown in FIGS. 2A and 2B measures exhaled airflow, in particular the amount of air and the rate of air that is breathed in and out over a specified period, such as for the forced expiratory volume over one second FEV1. It will be appreciated that while the approaches to detecting early changes in lung function as discussed herein are preferably thorough the use of the disclosed aerosol spirometer 100, they may be performed using any suitable aerosol generation device subject to cost, size, ease of use or related constraints.

In operation, the aerosol spirometer 100 permits the determination of a patient's breathing ability while the patient is engaged in tidal volume breathing. Significantly, such determination may be made in a home setting without recourse to complicated procedures, physical exertion or expensive equipment. In one mode, a single breath into the aerosol spirometer 100 is sufficient to acquire the data needed in order to make a fully-informed decision as to whether lung function has been compromised. Additional breaths can be used to improve the precision of the results or to gain greater insight into the nature of the breathing difficulties of the particular patient P, as well as to diminish the depositional losses of the exhaled aerosol concentration.

Figure 4:
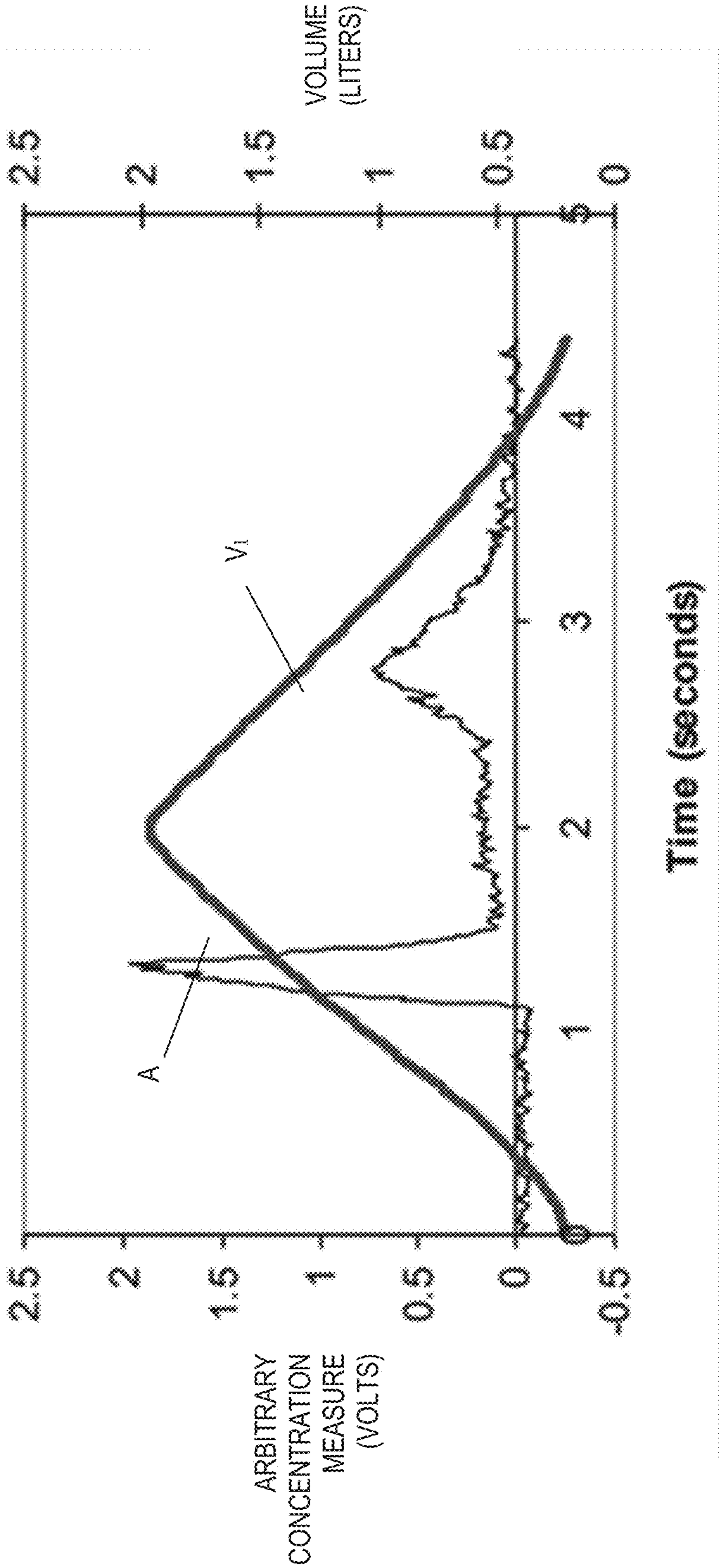
FIG. 4 depicts inhalation and exhalation portions of an actual breathing cycle measured as lung volume over time.

Referring next to FIG. 4, the author of the present disclosure discovered that significant inaccuracies associated with ventilation-based lung function testing could be attributed to both aerosol A loss within the respiratory tract 1 (such as through deposition) and penetration-based bolus profiles in the exhaled portion of each breath. To that end, these can be remedied by introducing the aerosol A in timewise short bursts, especially in the early part of the breathing cycle where otherwise diffuse aerosol A patterns can be avoided or minimized. In one particular form, measuring shorter, more rapid breaths decreases the likelihood that the known "first in/last out" exchange would skew the acquired data. As shown, a bolus of aerosol A is released into the breathing flowpath 102 by the aerosol dispersion mechanism 108 relatively early in the actual inhalation/exhalation cycle. The inhaled volume $V_1$ (in liters) shows both rising volumes (where the line is timewise on an upward slope during inhalation) and falling volumes (where the line is timewise on a downward slope during inhalation). Likewise, the leftmost spike in the aerosol A corresponds to it being introduced in a bursty manner roughly midway through the inhalation portion of the cycle, while the rightmost (and smaller) spike reflects concentration during the exhalation portion of the cycle. While such patterns present the breathing data in a rather straightforward way, the author of the present disclosure discovered that practical concerns over rapid patient P breathing patterns such as this may impose a burden on the patient P. To correct this, the patient P should be prompted to increase or decrease his or her breathing flow rate in order to decrease any deposition losses that would otherwise be detected in an initial series of breaths that are not included in producing data included in the overall analysis of the health of patient P. As will be discussed in conjunction with FIG. 6, a trained ML model made be built by a workflow that is made up of various preprocessing, feature extraction and statistical algorithms that operate on the data acquired by the aerosol spirometer 100 of FIGS. 2A through 2C in order to arrive at a suitable diagnostic or predictive analysis and that could take account for beathing flow rates and corresponding data patterns such as this. Such an approach can mimic the enhanced accuracy of the short breathing cycle with the ease of use of and patient P comfort of the presently-disclosed aerosol spirometer 100, as well as through the aerosol spirometry device disclosed in U.S. Pat. No. 7,241,269 the entirety of which is incorporated by reference in its entirety.

As such, a pulse of aerosol A can be released nearly instantaneously at a desired time during inhalation. Each of the individual particles of the aerosol A thereby becomes a timer, fixing the transit time (also referred to herein as aerosol dispersion transit time) upon exit from the lung 8. Referring again to FIGS. 2A and 2B, the sensor windows 114 are placed just outside the mouth of patient P for detection or measurement of the pulse of aerosol A for both inhaled and exhaled portions of the normal breathing cycle, where such detection is a function of breathing volume. The distribution of aerosol A transit times can then be displayed as the concentration distribution sensed and transmitted electronically for mathematical processing. As such, ventilation distribution within the lungs 8 impact aerosol A bolus dispersion in predictable, measurable ways.

Figure 5A:
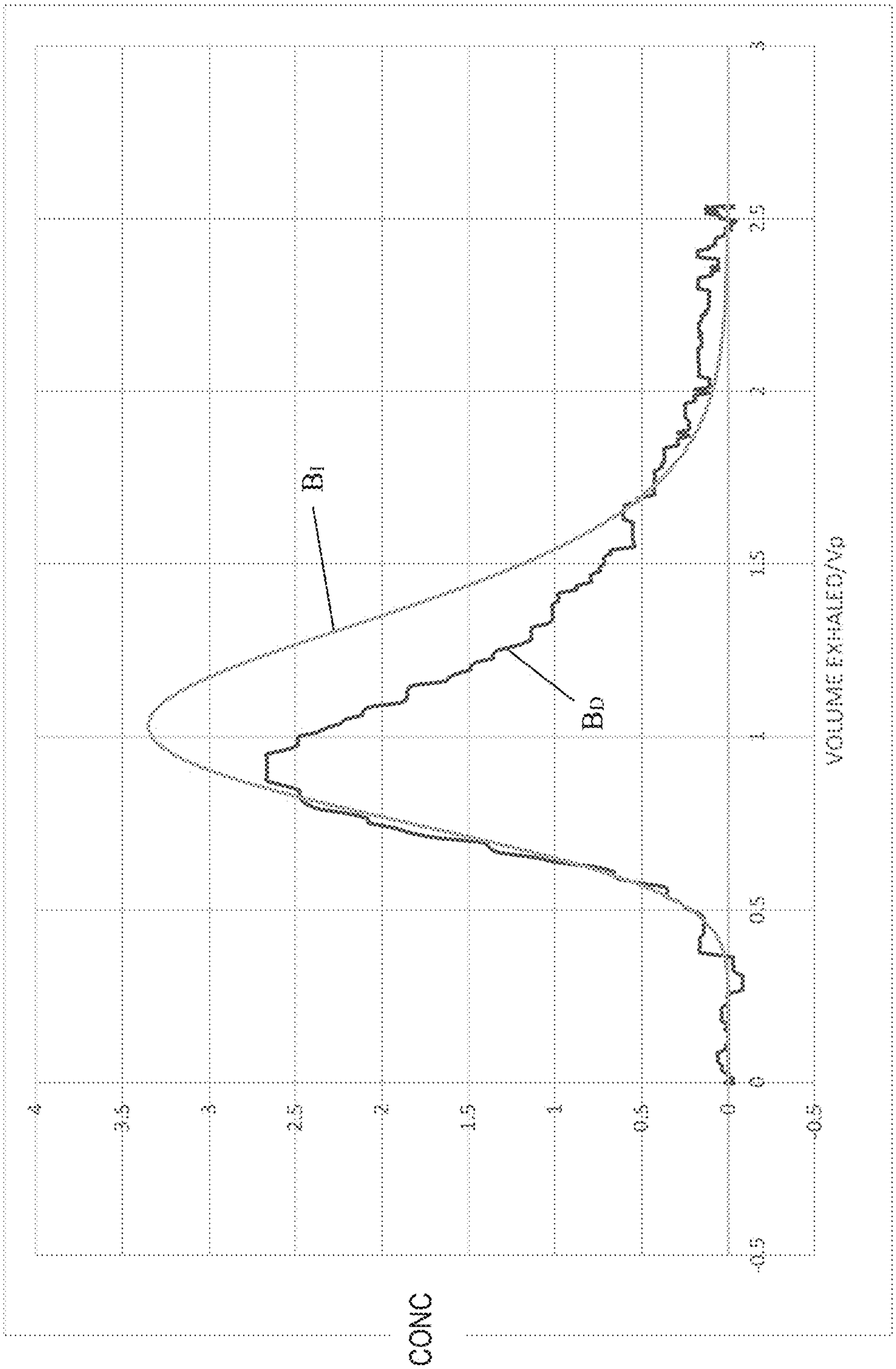
FIG. 5A depicts a comparison of an idealized exhalation aerosol concentration profile of the breathing cycle of FIG. 4 to actual data showing deposition-related loss in the data.
Figure 5B:
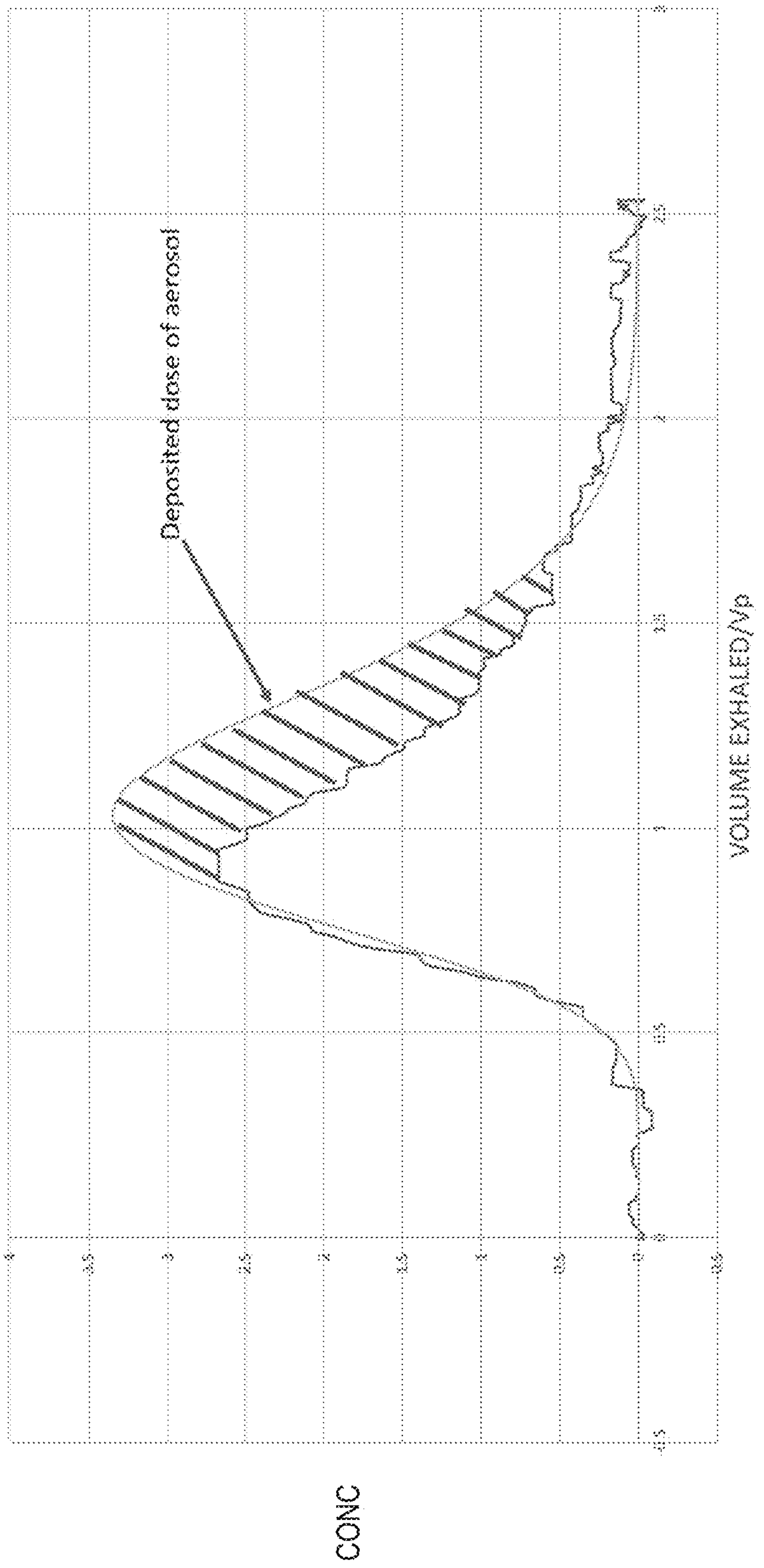
FIG. 5B depicts the estimated location (in terms of the inhaled lung volume) and amount of the deposited dose of aerosol in the lung from the output of the measurement of an exhaled bolus of aerosol in a patient's lung.

Referring next to FIGS. 5A and 5B, the author of the present disclosure further discovered that an exhaled aerosol A boli is missing significant amounts of data. In particular, FIG. 5A shows a comparison between an idealized breath $B_1$ and received breath data $B_D$. Without being bound by theory, the author believes that the missing data is attributed to the deposition of aerosol A onto lung 8 tissue. From here, an algorithmic analysis (including the those based on the ML models discussed herein) may be formed as a way to fill in the gaps associated with the missing data. In turn, air flow rate geometry and expected volume may be described and in turn adjusted with empirical data acquired through the aerosol spirometer 100. At the volume of penetration where the lung model and the data from the aerosol bolus inhalation differ aerosol loss through deposition is assumed to be the mechanism for such a deviation. The deposition is assumed to be due to an obstruction of the airflow, enhancing impaction and sedimentation loss and thus designating the volume at which the obstruction is occurring. Not only does this improve the ability to predict certain lung functions with aerosol spirometry, but also assists in pinpointing a particular location within the lung 8 where restrictions or obstructions are taking place. In the particular instance shown, the jagged line is actual data (i.e., the aforementioned received breath data $B_D$) with a measured deposition rate of 22.6%. As such, the signal remaining represents only 77% of possible information. The smooth line is a hypothesized fit of a model equation (that is to say, an idealized exhalation aerosol concentration profile (also referred to herein as concentration distribution when accounting for the numerous calculated aerosol dispersion transit times) that has been fit to data prior to that portion of the exhaled data at an exhaled (dimensionless) volume. It will be appreciated that the obstruction discussed herein may be determined with greater specificity (such as through identification of the location in the graph where the two profiles diverge) than that possible from the device and methods of the aforementioned U.S. Pat. No. 7,241,269.

By way of example, parameters of the algorithm may be used to convert the aerosol dispersion data to correlated values of flow-volume spirometry, thereby translating the parameters into CDS values or others with which the physician, nurse or other caregiver is both knowledgeable and comfortable. In this way, the transition from old (and mostly inappropriate flow volume spirometry) variables to new (aerosol spirometry) values is eased. One manner of corelating these algorithmic values to flow volume spirometry values may be found in an article by McCawley et al. entitled *Comparison of the Measurement of Obstructive Pulmonary Disease Using Spirometry, Plethysmography and Aerosol Dispersion Techniques* (*EC Pulmonology and Respiratory Medicine* 8.2 (2019)) the entirety of which is hereby incorporated by reference. It will be appreciated that the loss of exhaled aerosol signal leads to erroneous values as well as erroneous translation to former values, and that the device and methods of the present disclosure are significant in avoiding these lost signals to the extent possible.

Significantly, the acquired data may be used for lung 8 mapping that in turn can be correlated to such pinpointing. Moreover, such mapping will be useful for the subsequent introduction of a particular medicament or related pharmaceutical agent. In this, way, possible inaccuracies such as those based on introducing larger-sided compaction-based aerosols A may be accounted for, particularly with the use of small, sedimentation-based aerosols A where the known effects of gravity and associated gradients in airway compliance may be taken into consideration in showing that the lower portions of the lungs 8 may be receiving an inordinate amount of aerosol A. In other words, because lung ventilation is impacted by gravity, gradients in airway compliance (that is a measure of lung elasticity) occurs, which in turn means that not all alveoli 11 fill at the same rate or time. This in turn can be correlated to striated or related spatially-varying time constants for the various individual pathways. This in turn can affect the distribution of the aerosol A tracer by constraining some portion of both the breathed air and the aerosol A, thus changing the "first in/last out" sequence and the distribution of the aerosol A tracer concentration. This result will also be dependent on the volume at which the tracer is inserted as well as the time constant for a given pathway.

The product of the two mechanical components-resistance R and compliance C—of the airways of the lungs 8, when taken together, determine the functional ability of the lungs 8 to ventilate through the ability to extract time from their respective quantities:

$$R = \frac{\Delta P * t}{\Delta V}$$

and $$C = \frac{\Delta V}{\Delta P}$$

where P equals pressure, t equals time, and V equals volume. This dimensional analysis reveals that the units of the product of compliance C times resistance R cancel out, leaving time t as the only remaining dimensional unit. In this way, the breathing process may be modeled more as a mechanical system rather than a chemical one. Relatedly, the precise location-based information may be used to correlate to a more accurate and comprehensive understanding of mapping of the lung 8. From this, a more targeted medicament delivery protocol may be undertaken, particularly as it relates to the size of medicament-laden aerosol A being introduced.

The author of the present disclosure notes that the approach disclosed herein can be replicated and averaged over multiple breaths, therefor providing (for patients who can tolerate repeated breath testing) significant increases in data that in turn may be useful for averaging purposes as a way to enhance the precision and sensitivity of any measurement utilizing it. Importantly, traditional flow-volume spirometry cannot replicate this. The author of the present disclosure also notes that while the device and methods disclosed herein may (or may not) have direct applicability for cancer detection, it may be useful in detecting certain heart-related maladies, such as congestive heart failure.

As previously mentioned, aerosol dispersion is caused by differences in the resistance R and compliance C between inhalation and exhalation of the various pathways in the lung. Among a sample set of healthy individuals, there is relatively little variability in those differences in resistance R and compliance C between subjects, which in turn leads to consistent aerosol dispersion values in healthy subjects. Contrarily, changes in resistance R or compliance C in diseased portions of the lung of individuals with obstructive or restrictive lung disease such as asthma, bronchitis, emphysema and other fibrotic tissue diseases manifest themselves as significant changes in aerosol dispersion.

Significantly, the aerosol spirometer 100 offers various options to the clinician for testing the patient, such as—desired volume of penetration of the bolus, number of breaths to test and volume above or below functional residual capacity at which to begin determining penetration volume. The aerosol spirometer 100 can then collect the data and send it to a separate computer for analysis including—as previously noted—predictive analytics based on a data-derived ML model. In one particular form, the lung function test includes using a tidal-volume, relaxed, breathing maneuver with an aerosol bolus (0.7 μm corn oil) delivered during approximately 5 milliseconds of an assumed 2 to 3 second inhalation at a selectable volume before the end of inhalation. Both inhaled and exhaled concentrations of aerosol A are monitored using the sensor windows 114 of FIGS. 2A and 2B. The exhaled concentration distribution is a function of the combined resistance R and compliance C components of the airways and represents the difference between inhalation and exhalation in parallel and sequential mixing of the lung regions through which the bolus passed. As noted in the previous dimensional analysis, time t is the only remaining dimensional unit. Analysis can therefore be done by determining the concentration distribution as a function of time t, adjusted for flow by using volume V as a surrogate for time t. Each particle within aerosol A acts as a timer describing the time constant for the path it followed. Significantly, the distribution of these timers represents the distribution of the mechanical function of each lung unit or pathway, that is, the combined compliance C and resistance R of the airways.

Figure 6:
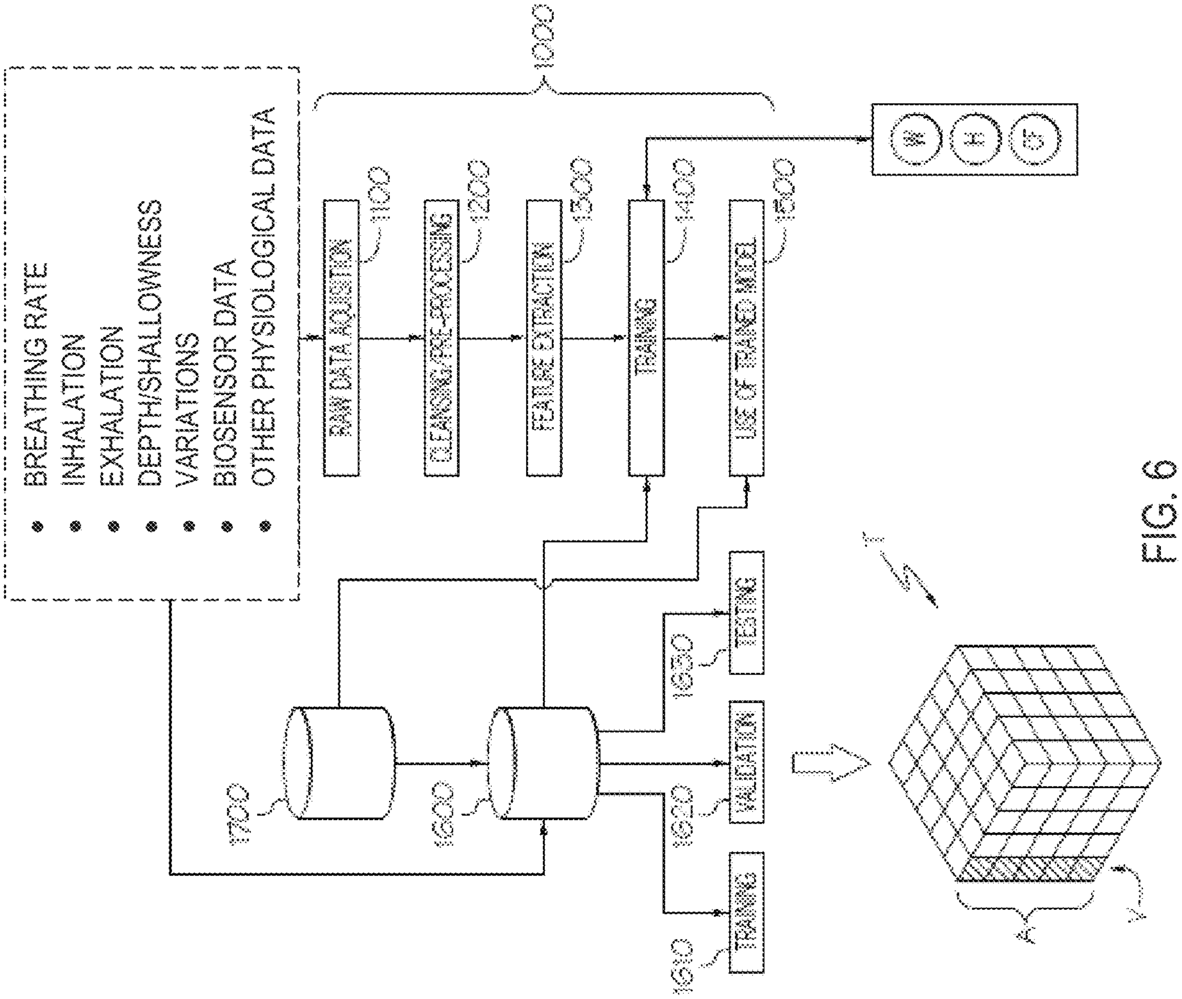
FIG. 6 depicts an ML-based canonical workflow for training an ML model using the lung function data that has been collected by the aerosol spirometer of FIGS. 2A through 2C and 3A through 3D.

As previously noted in FIGS. 2A through 2C, the controller 116 may form the basis of an ML model using the data acquired by the aerosol spirometer 100. Referring next to FIG. 6, a program structure in the form of a flow diagram of how the aerosol spirometer 100 and controller 116 may be used to develop the ML model through an ordered sequence (which is referred to herein as an ML workflow 1000) that may include the following steps: (1) a raw data acquisition (first) step 1100; (2) a raw data cleansing or otherwise preprocessing (second) step 1200, such as through the use of signal processing via noise filters, normalization or the like as a way to separate out various redundancies and related noise in order to process only the data that will bring about a statistically significant increase in predictive or explanatory power; (3) a feature extraction (third) step 1300 of derived values which may include placing the data into the previous-mentioned feature vector or related form, and which may involve some form of data mining or related exploratory data analysis; (4) a training (fourth) step 1400 for application of an iterative ML algorithm to fit or create the model; and (5) a model use or inference (fifth) step (that is to say, trained ML model) 1500 with which to operate the trained ML model 1500 on some or all of the acquired data in order to draw inferences (for example, directing breathing rates to reduce exhaled aerosol loss) from such data. In one form, this ordered sequence may be used to provide predictive analytics to assist in the diagnosis by doctors, nurses and other caregivers of a particular lung dysfunction of the individual P. In another form, the ordered sequence may be used to perform its own autonomous diagnosis without human intervention. In yet another form, this ordered sequence may be used to perform an action plan so that it can provide guidance on changes in a care plan. Moreover, because such diagnosis is based on the acquired data that is specific to a particular individual patient P, such diagnosis and the ensuing action plan could qualify as personalized medicine and related individualized-profile clinical decision-making. The first three steps 1100, 1200, 1300 form the core of data management, while the last two steps 1400, 1500 lead to learning, inference or related analytics to acquire intelligence from the initial voluminous data set. As such, it will be appreciated that the first three steps 1100, 1200, 1300 may be performed independently—as well as part of—an ML-based analysis, and that both variants are within the scope of the present disclosure. It will further be appreciated that ML workflow 1000 depicted herein is notional, and that it may be modified according to the type of machine learning algorithm or resulting model that are listed in more detail elsewhere in this disclosure.

In one form, one or both of baseline data 1700 and presently-acquired data 1600 may be stored in memory 116C in an unstructured, flat file format such that during the cleansing or related preprocessing associated with the second step 1200 of the ML workflow 1000, improvements in data uniformity may be realized. In one form, grouping the acquired data can be through an unsupervised clustering model; such an approach may be particularly good at segmenting the data into several different groups. In one form, this baseline data 1700 may be annotated for use in training-based activity, behavior or related parametric information that can be compared to real-time (i.e., presently-acquired) data in turn can be operated upon by one or more of the ML models 1500 discussed herein. The baseline training examples may include representative temporal sequences, including being further annotated or labeled in order to be scene-specific or situation-specific as a way to provide context for the model, as well as for model training. As shown by the three-dimensional representation of data in the figure, any or all forms of data may be expressed as a vector V (which may be considered as a one-dimensional tensor), array A (or matrix and which may be considered as a two-dimensional tensor) or multidimensional array (that is to say, a data structure the represents a tensor T (which itself is a type of function) in a given coordinate system) in order to be in appropriate feature vector form for subsequent use of the independent data. Although shown as a cubic three-dimensional representation in the figure, it will be appreciated that tensor T may possess a greater number of dimensions depending on the needs of the training or other data set. Some of the data being acquired (such as through the raw data acquisition step 1100) may relate to breathing rate, inhalation quantities, exhalation quantities, depth or shallowness of breath, varying periods of breathing, respiratory sounds associated with certain breathing patterns, moisture content, biosensor data (such as from an electrocardiogra (ECG), electroencephalography (EEG), optical photoplethysmography (PPG) or the like, as well as activity or other physiological processes associated with patient P), as well as patterns or related quantities that may be algorithmically determined from one or more of these forms of raw data. It will be appreciated that the foregoing list is representative, not exhaustive. As such, other forms of breathing-related data known to those skilled in the art are deemed to be within the scope of the present disclosure.

As part of the cleansing or preprocessing second step 1200, the acquired data may be tagged or identified, including through the use of spatio-temporal identifiers including location, time stamp, sensor class (for example, temperature, pressure or the like) or unique sensor identification codes. Data acquisition libraries, such as those available from MATLAB may be used to provide sensor-based data acquisition support for such tagging and identification; such support may include other forms of data preprocessing, including class-labeling, noise filtering and related cleansing or scrubbing, as well as data balancing, all as a way to transform the data into a form that may be used by the subsequent feature extraction, algorithm selection, training and eventual predictive analytics model usage. In one example, the acquired data that has been operated upon by some or all of these libraries may be subjected to receiver operating characteristic (ROC) analysis as a way to quantify the performance of an activity classification algorithm. In one form, such an analysis may be in the form of a curve to provide visual comparison between various classification models where the area under the ROC curve (AUC) provides a measure of a particular model's accuracy. This model evaluation, which takes place once a model is tested and evaluated, may also be based on other criteria such as mean squared error, accuracy, sensitivity, specificity or the like. In this way, the activity classification algorithm can use known diagnostic performance metrics such as ROC and area under the ROC curve (AUC) values, positive and negative predictive value, sensitivity, specificity or the like to allow a comparison against physician-based expert diagnoses. Such an approach may be particularly beneficial when there are imbalances in the classes of data being used as part of a particular data set.

In one form, filters may be applied to control data sampling rates or the like. In one form, statistical-based feature extraction may be used on the acquired raw data such that the resulting set of such features may be presented for use as input in a subsequently-created ML model 1500. In one form, the feature extraction of sensed data may be accomplished through adders, multipliers, impulse filters, band-pass filters or related mathematical operation circuitry contained within the processor 116B or elsewhere. For example, peak analysis may be used to find important frequency content, such as through Fast Fourier Transform or the like.

While it is understood that different kinds of data may involve different methods for the cleansing or preprocessing second step 1200, there are some methods that tend to be employed for almost all forms of data, including the lung function-related data which is discussed herein. As part of this second step 1200 of the ML workflow 1000, the data that is being acquired by the aerosol spirometer 100 may be filtered, amplified and converted wherever the controller 116 is located, that is to say, either at the edge or at a centralized location such as the cloud 116G. For example, the acquired data may go through a normalization process in situations where features (that is, the columns within a matrix or array of data) have different ranges. With normalization, the numeric values of the data are adjusted to a common scale while substantially preserving differences in the ranges of values in order to avoid gradient upsets (and a consequent failure to converge) during subsequent optimization steps. In addition, the acquired raw data is typically transformed into vectors or related meaningful numeric representation, as discussed elsewhere within the present disclosure. Thus, for every row of a particular type of data is converted into suitable integer values as a way to populate an input matrix. Furthermore, the data may be spare and therefore have missing values, in which either zero-value or interpolated mean value placeholders may be inserted into the respective column of the matrix.

As previously mentioned, such cleansing or preprocessing second step 1200 need not be a part of a n ML-based approach, and instead may be used for other forms of analysis where improvements in data uniformity and manageability are needed. Regardless of whether the various forms of data cleansing and other manipulation are used in an ML-based approach or not, the architecture of the aerosol spirometer 100 is such that it not only improves the operation and efficiency of the reception and transmission of various forms of data, but also of the data gathering itself in that by acting as a single point for data gathering, the aggregation of the data gathering and dissemination need not be dispersed over larger portions of a network. This in turn helps promote consistency of the data. Moreover, by providing a singular, unitary platform (such as through the housing 104-based containment structure discussed previously in conjunction with FIGS. 2A through 2C), the aerosol spirometer 100 is able to provide for a relatively unobtrusive user experience.

This second step 1200 of the ML workflow 1000 is also useful in making subsequent analytic inferences from the data more tractable. For example, redundancy and size of an initial set of raw features taken from the sensed data can make such data difficult to manage, especially as it relates to providing a meaningful way to classify a particular lung 8 condition. In particular, the acquired data is often diverse and complex, even for the same person P during different testing times. The amount of information associated with such baseline data 1700, as well as subsequently-acquired data that is taken from the various sensors of the aerosol spirometer 100, is potentially voluminous, and often of a heterogeneous nature. In addition to ensuring that the data is uniform as a prerequisite for rendering it useful for its intended purpose of extracting ML insights, another prerequisite may be to reduce its dimensionality. Such dimensionality reduction may be seen as a portion of the second step 1200 of the ML workflow 1000 five-step ordered sequence. In one form, the data interpretation may be performed by one or more portions of machine code that are operated upon by the processor 116B such that output of the analysis is provided for use by the patient P or a caregiver. In one form, the results of the analysis that are associated with such output may be stored in memory 116C, as well as provided in transient, real-time to a display, audio device, graphical user interface (GUI) or the like all of which may form a part of the user interface 116A.

In one form, the process of converting the raw data into a form suitable for use in an ML algorithm and subsequent model 1500 may form part of an activity known as extraction, transformation and loading (ETL) that may make up part of the previously-discussed second and third steps 1200, 1300 of the ML workflow 1000. Within the present context, ETL may be used to decompose multi-sensor data into a suitable feature vector within a given feature space that can then be correlated through subsequent fitting and evaluation of the fourth and fifth steps 1400, 1500 of the ML workflow 1000 in order to produce one or more model-based performance metric results for certain types of predictive analytic activities, such as those associated with lung function determination or prediction. By way of example, a feature space in two dimensions may be represented through the two axes of a common x-y graph, while additional representations along a third axis (for example, the z-axis) may be made to correspond to outputs, such as those of one of more hidden layers in a neural network in order to define a feature space in three (or more) dimensions in a manner analogous to a tensor. Within the present disclosure, the term "converting" and its variants are understood to include all steps necessary to achieve ETL functionality, including cleansing of the data or reducing its dimensionality the latter of which may be in the form of feature selection.

The models employed by system 1—which may include machine code that can be written in or converted from one of several programming languages such as Python, Java, R or the like—as well as employing their corresponding ML libraries or toolkits, such as MATLAB, NumPy, Weka, kernlab, SciPy, LIBSVM, SAS, SVMlight, Scikit-Learn, JKernalMachines, Shogun or others-engage in iterative approaches to update the decision-making process as a way to learn from the various forms of data being acquired by the aerosol spirometer 100. For example, an ML library such as Scikit-learn is used with the Python programming language to provide various classification, regression and clustering algorithms including support vector machine, random forests or others. In addition, it operates in conjunction with Python numerical and scientific libraries NumPy and SciPy. Moreover, APIs (such as TensorFlow, $H_2O$, Spark MLlib or the like) may be used to help determine the best ML model 1500 to use, while some of the libraries mentioned above may include unified APIs to facilitate ease of use of a particular ML model 1500. In one form, an open-source ML core library such as NumPy is used for performing fast linear algebra and related scientific computing within the Python programming language. NumPy provides support operations for multidimensional array and matrix (but not on scalar quantities) data structures, along with a large collection of high-level mathematical functions to operate on these arrays. For example, the linear equations that represent linear algebra are presented in the form of matrices and vectors that may be memory-mapped as data structures for computing complex matrix multiplication relatively easily. Because the data that is being acquired by the aerosol spirometer 100 is multidimensional and takes place over time for the same patient P, multidimensional data structures known as Pandas (that is to say, PANel DAta Sets) may be used for the initial data preprocessing. As will be discussed in more detail later, such data may be input into vectors such as Pandas data structures (also referred to as dataframes) or NumPy arrays such that they can later be broken up into training data sets, validation data sets and test data sets for ML use.

Moreover, it is possible through feature extraction-based parameter-reduction techniques such as gradient descent, backward propagation (also referred to herein as backpropagation) or the like to prune a network (such as a deep learning neural network) and improve the mapping between data input and output to achieve minimized cost functions associated with classifying the corresponding lung condition being predicted. Thus, at least in supervised versions of the ML model 1500, feature extraction takes advantage of knowledge already known to help provide those predictive features most likely of use for a physician or other caregiver C in order to make a clinical diagnosis. Such reduction techniques, as well as those associated with convolutional weighted kernels, filters, channels or the like, are additionally helpful in their ability to reduce the processor 116B and memory 116C requirements associated with deep learning algorithms and models, thereby allowing them to operate with significant reductions in computational and storage power.

Within the ML context, various analogies and terms may be useful in understanding how the data that is being acquired by the aerosol spirometer 100 may be correlated to information pertaining to the lung condition of patient P. For example, terms related to the data being acquired, analyzed and reported include "instance", "label", "feature" and "feature vector". An instance is an example or observation of the data being collected, and may be further defined with an attribute (or input attribute) that is a specific numerical value of that particular instance, while a label is the output, target or answer that the ML algorithm is attempting to solve, the feature is a numerical value that corresponds to an input or input variable in the form of the sensed parameters, whereas a feature vector is a multidimensional representation (that is to say, vector, array or tensor) of the various features that are used to represent the object, phenomenon or thing that is being measured by the aerosol spirometer 100. Visually, the instance, label and feature can populate a data table (or spreadsheet) such as the previously-mentioned x-y graph or x-y-z graph where the instances may be listed as numerous rows within a single label column, whereas the features populate various labeled columns for each row. To think of it colloquially, the use of ML model 1500 to solve a classification, regression or other problem can be analogized to preparing a meal, where (a) the data being acquired by the aerosol spirometer 100 corresponds to the ingredients to be used, (b) the mathematical code that is the algorithm is a sequence of actions that may be analogized to the tools, equipment, appliances or the like that operates on the ingredients, (c) the ML model 1500 is the recipe that is used in conjunction with the algorithmic tools to provide a framework for repeatability and (d) the label is the desired output in the form of the finished dish. Thus, the ML model 1500 may be understood as the recipe that is formed by using the correct number and quantity of ingredients from the data that have been subjected to trial-and-error training through the use of the tools that make up the algorithm. As such, the ML model 1500 is a mathematical description of how to convert input data into a labeled output; a new model 1500 may be generated with the same algorithm with different data, or a different model 1500 may be generated from the same data with a different algorithm. Thus, within the context of ML, the algorithms discussed herein are constructed to learn from and make predictions in a data-driven manner based on the data being acquired by the aerosol spirometer 100, and from these algorithms, the model 1500 may be built for subsequent use in identifying salient indicators of the health of the lung 8 for the patient P that is using the aerosol spirometer 100. In this way, the ML model 1500 is the resulting output once an ML algorithm has been trained by the acquired data.

In one form, the feature vectors (which may occupy a corresponding feature space) are subjected to a scalar multiplication process in order to construct a weighted predictor function. Moreover, feature construction may be achieved by adding features to those feature vectors that have been previously generated, where operators used to perform such construction may include arithmetic operators (specifically, addition, subtraction, multiplication and division), equality conditions (specifically, equal or not equal) and array operators (specifically, maximums, minimums and averages) among others. In one form, the analytics associated with these feature vectors may be performed in order to ascertain classification-based results (for example, whether the sensed parameter or attribute is less than, equal to or greater than a threshold that may itself be based on a known relative baseline, absolute baseline or other measure of interest), or to perform a regression in order to determine whether the sensed parameter or its attribute can be correlated to the likelihood of an event outcome. Within the present context, a feature vector could be a summary of such data such that the ensuing clinical observation of symptoms may lead to an enhanced diagnosis of a particular lung condition as discussed herein.

In one form, some or all of the program structure that defines the last three steps 1300, 1400, 1500 (that is, feature extraction, algorithmic training and use of the subsequent model to generate useful analytical output or prediction) of the multistep ML workflow 1000 may be embodied in machine code. In this way, particular forms of data extraction may be performed through the manipulation of this data through the cooperation of the processor 116B and the machine code, as can one or more of the ML algorithms discussed herein for use with the training and subsequent ML model 1500 analysis. As such, the use of ML the aerosol spirometer 100, or whether given that such condition is already present, whether it is becoming worse.

As can be seen from the foregoing, for the ML portion of the analysis, certain canonical approaches may be used as part of the ML workflow 1000 in order to train the resulting model 1500. While not being bound by theory, and further in recognizing that many ML algorithms (including, but not limited to, k-nearest neighbors (kNN), neural networks (including convolutional neural networks (CNNs) and its deep learning variants such as recurrent neural networks (RNNs)), hidden Markov approaches, naïve Bayes, decision trees (such as classification and regression trees (CART) or C4.5), ensemble methods (including boosting, bootstrap aggregating (bagging) and random forest), support vector machines, other Bayesian approaches, regression-based approaches, clustering approaches (such as K-means clustering), dimensionality reduction approaches (such as principal component analysis (PCA) or linear discriminant analysis (LDA), Markowitz-based approaches, recurrent approaches which may be further grouped into, among others, perceptrons, sequential/recurrent, long short-term memory (LSTM), Hopfield, Boltzmann machines, deep belief networks, auto-encoders or the like), reinforcement learning, cross-validation and stochastic gradient descent, as well as combinations thereof) are available for use, the author of the present disclosure has recognized that in situations where the acquired data is sparse or intermittent, certain ML algorithms generally perform better than others. For example, support vector machines and random forest have generally performed well with sparse datasets, while RNN and LSTM may be used for temporal-based events such as breathing.

In addition to some of the various cleansing, extracting and related canonical operations associated with the aforementioned ML workflow 1000, the data may be smoothed in order to obtain continuous data, or to fit it to the idealized exhalation aerosol concentration profile in order to produce a data-informed exhalation aerosol concentration profile that in one form may be an updated exhalation aerosol concentration profile. In such case, the smoothing techniques may be used to acquire standard deviation values and a more continuous data flow that may then be subjected to a distribution fitting test (such as decision trees, Chi square test or Anderson-Darling tests) in order to determine a data distribution that forms a good continuous data curve fit. In such case, other ML algorithms, such as some of the aforementioned ensemble-based approaches, may be used on the continuous data in order to obtain one or more calculated values. These calculated values may then be the basis for the data-informed exhalation aerosol concentration profile from which a prediction may be made of a lung condition based on a correlation between such profile and various symptoms that are indicative of a lung function. From this, the controller 116 may transmit the predicted lung condition to a user, such as a patient, nurse, physician or other interested individual. In one particular form, the trained ML model 1500 forms an inference engine in order to generate predictive or probabilistic outputs. In this way, the previously noted databases, registries or related references may be updated by the inference engine, including those that take into consideration the sizes of the databases as a way to calculate deductive and empirical probabilities. By way of example, the inference engine for determining event probability may be based on a Bayesian classifier approach, such as to use weighting schemes to adjust the classifier based on cost function-related errors. In this way, the inference engine may further be used to test hypotheses about the efficacy of potential courses of treatment for patient P in particular or demographically similar patients. Moreover, by using a Bayesian-based approach (particularly a naïve Bayes approach) may help reduce the number of iterations in the training step 1400 that in turn reduces computational complexity and the need for associated resources.

In one form, the aerosol spirometer 100 of FIGS. 2A through 2C and 3A through 3D may be combined with the ML model 1500 to form a system 2000 that can detect early changes in lung function. As mentioned elsewhere in the present disclosure, the system may be used to adjust time constants (such as aerosol dispersion transit times) based on penetration and deposition inhomogeneities. In this way, losses within the exhalation portion of a normal breathing cycle may be accounted for to adjust these time constants and therefore provide a more complete concentration distribution of the detected plurality of aerosol particles contained within the normal breathing cycle.

Within the present disclosure, one or more of the following claims may utilize the term "wherein" as a transitional phrase. For the purposes of defining features discussed in the present disclosure, this term is introduced in the claims as an open-ended transitional phrase that is used to introduce a recitation of a series of characteristics of the structure and should be interpreted in like manner as the more commonly used open-ended preamble term "comprising" and its variants that do not preclude the possibility of additional acts or structures.

Within the present disclosure, terms such as "preferably", "generally" and "typically" are not utilized to limit the scope of the claims or to imply that certain features are critical, essential, or even important to the disclosed structures or functions. Rather, these terms are merely intended to highlight alternative or additional features that may or may not be utilized in a particular embodiment of the disclosed subject matter. Likewise, it is noted that the terms "substantially" and "approximately" and their variants are utilized to represent the inherent degree of uncertainty that may be attributed to any quantitative comparison, value, measurement or other representation. As such, use of these terms represents the degree by which a quantitative representation may vary from a stated reference without resulting in a change in the basic function of the subject matter at issue.

Within the present disclosure, the use of the prepositional phrase "at least one of" is deemed to be an open-ended expression that has both conjunctive and disjunctive attributes. For example, a claim that states "at least one of A, B and C" (where A, B and C are definite or indefinite articles that are the referents of the prepositional phrase) means A alone, B alone, C alone, A and B together, A and C together, B and C together, or A, B and C together.

Within the present disclosure, the following claims are not intended to be interpreted based on 35 USC 112 (f) unless and until such claim limitations expressly use the phrase "means for" or "steps for" followed by a statement of function void of further structure. Moreover, the corresponding structures, materials, acts and equivalents of all means or step plus function elements in the claims below are intended to include any structure, material or act for performing the function in combination with other claimed elements as specifically claimed.

Within the present disclosure, the singular forms "a," "an" and "the" include plural references unless the context clearly dictates otherwise. The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6 to 9, the numbers 7 and 8 are contemplated in addition to 6 and 9, and for the range 6.0 to 7.0, the number 6.0, 6.1, 6.2, 6.3, 6.4, 6.5, 6.6, 6.7, 6.8, 6.9 and 7.0 are explicitly contemplated.

The present description is for purposes of illustration and is not intended to be exhaustive or limited. Many modifications and variations will be apparent to those of ordinary skill in the art without departing from the scope and spirit of the present disclosure. Aspects of the present disclosure were chosen and described in order to best explain the principles and practical applications, and to enable others of ordinary skill in the art to understand the subject matter contained herein for various embodiments with various modifications as are suited to the particular use contemplated.

Unless otherwise defined, all technical and scientific terms used herein that relate to materials and their processing have the same meaning as commonly understood by one of ordinary skill in the art. In case of conflict, the present document, including definitions, will control.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method of performing an aerosol dispersion-based respiratory system test, the method comprising:

configuring an aerosol spirometer to introduce an aerosol into a respiratory system;

upon receipt within the aerosol spirometer of an inhalation portion of a normal breathing cycle from a patient, providing an aerosol pulse such that the aerosol pulse mixes with ambient air from the inhalation portion;

detecting, with the aerosol spirometer, a plurality of aerosol particles contained within the inhalation portion;

detecting, with the aerosol spirometer, a plurality of aerosol particles contained within an exhalation portion;

reducing losses within the exhalation portion that are attributable to at least one of aerosol impaction and sedimentation through:

creating a data-informed exhalation aerosol concentration profile by comparing a distribution of the detected plurality of aerosol particles contained within the exhalation portion to an idealized exhalation aerosol concentration profile; and populating the idealized exhalation aerosol concentration profile with at least a portion of additional detected plurality of aerosol particles contained within the normal breathing cycle such that an updated exhalation aerosol concentration profile with reduced losses is created;

calculating aerosol dispersion transit times of the detected plurality of aerosol particles contained within the normal breathing cycle, wherein at least a portion of the calculated aerosol dispersion transit times is based on the reduced losses;

determining a concentration distribution of the detected plurality of aerosol particles contained within the normal breathing cycle based on the calculated aerosol dispersion transit times;

transmitting a signal that corresponds to the concentration distribution of the detected plurality of aerosol particles contained within the normal breathing cycle to a processor-based controller; and determining whether the respiratory system is suffering from an adverse lung condition based on a correlation between a plurality of symptoms indicative of a lung function to the concentration distribution.

2. The method of claim 1, wherein comparing the distribution of the detected plurality of aerosol particles to an idealized exhalation aerosol concentration profile and populating the idealized exhalation aerosol concentration profile with at least a portion of additional detected plurality of aerosol particles comprises a distribution fitting test that is selected from a statistical model comprising at least one of a gamma distribution, a normal distribution, a Poisson distribution and negative binomial distribution.

3. The method of claim 2, wherein a portion of at least one of the calculating, determining and creating are performed with a trained machine learning model.

4. The method of claim 1, wherein the aerosol spirometer defines a portable form factor.

5. The method of claim 4, wherein the portable form factor comprises a handheld device.

6. The method of claim 1, wherein the lung function comprises at least one of asthma, bronchitis, cystic fibrosis, chronic obstructive pulmonary disease (COPD), emphysema and combinations thereof.

7. The method of claim 1, wherein the concentration distribution of the detected plurality of aerosol particles is performed using time constants that are based on a directly measuring lung compliance and lung resistance throughout a plurality of locations within the lung.

8. The method of claim 1, wherein the data-informed exhalation aerosol concentration profile is based on at least one of aerosol penetration and aerosol deposition within a plurality of locations within the lung.

9. The method of claim 1, wherein at least some of the aerosol particles that are introduced by the aerosol pulse define a diameter of between about 0.5 μm and 0.7 μm.

10. A machine learning-based system for analyzing lung function, the system comprising:

an aerosol spirometer; and a computer with at least one processor and a non-transitory computer readable medium storing machine-readable instructions that cause the at least one processor to:

receive a plurality of data points from the aerosol spirometer, the plurality of data points corresponding to aerosol particles that have been introduced by the aerosol spirometer into the lung of an individual for traversal therethrough;

determine a time-based indication of at least one of aerosol deposition and aerosol penetration within the lung, wherein the time-based indication corrects for losses within an exhalation portion of a normal breathing cycle through a data-informed exhalation aerosol concentration profile that is based on a comparison of a distribution of the plurality of data points to an idealized exhalation aerosol concentration profile such that the idealized exhalation aerosol concentration profile becomes populated with at least a portion of additional data points such that an updated exhalation aerosol concentration profile is created;

predict a lung condition based on a correlation between a plurality of symptoms indicative of a lung function of the lung to the updated exhalation aerosol concentration profile; and transmit the predicted lung condition to a user.

11. The machine learning-based system of claim 10, wherein the aerosol spirometer defines a handheld form factor wherein at least one of the aerosol bolus delivery flowpath and the at least one particle sensor are secured to the handheld form factor.

12. The machine learning-based system of claim 10, wherein the distribution is selected from a statistical model comprising at least one of a gamma distribution, a negative binomial distribution, a normal distribution and a Poisson distribution.

13. The machine learning-based system of claim 12, wherein the statistical model comprises a moment analysis that utilizes the mean (first moment), standard deviation (second moment) and skewness (third moment).

14. The machine learning-based system of claim 10, wherein the distribution comprises a distribution fitting test comprising at least one of an Anderson-Darling test, Boltzmann distribution Chi square test, F-distribution, Gaussian distribution, half-normal distribution, inverse Gaussian distribution, negative binomial distribution, Poisson distribution, Rayleigh distribution, Weibull distribution and a decision tree.

15. The machine learning-based system of claim 10, wherein the trained machine learning-model is based on at least one of a random forest algorithm, a support vector machine algorithm and a Bayesian algorithm.

16. The machine learning-based system of claim 10, wherein the trained machine learning-model further uses the at least one of the aerosol deposition and aerosol penetration to select data to be fitted to the idealized exhalation aerosol concentration profile.

17. A method of performing an aerosol dispersion-based respiratory system test on a patient, the method comprising:

configuring an aerosol spirometer to introduce an aerosol into the respiratory system;

upon receipt within the aerosol spirometer of an inhalation portion of a normal breathing cycle from the patient, providing an aerosol pulse such that the aerosol pulse mixes with ambient air from the inhalation portion;

detecting, with the aerosol spirometer, a plurality of aerosol particles contained within the inhalation portion;

detecting, with the aerosol spirometer, a plurality of aerosol particles contained within the exhalation portion;

calculating, using a machine learning model, aerosol dispersion transit times of the detected plurality of aerosol particles, wherein data points representative of the aerosol dispersion transit times corrects for losses within the exhalation portion of a normal breathing cycle through a data-informed exhalation aerosol concentration profile that is based on a comparison of a distribution of the plurality of data points to an idealized exhalation aerosol concentration profile such that the idealized exhalation aerosol concentration profile becomes populated with at least a portion of additional data points such that an updated exhalation aerosol concentration profile is created;

determining a concentration distribution based on the updated exhalation aerosol concentration profile;

transmitting a signal that corresponds to the concentration distribution to a processor-based controller; and determining whether the respiratory system is suffering from an adverse lung condition based on a correlation between a plurality of symptoms indicative of a lung function to the concentration distribution.

18. The method of claim 17, wherein the determining the location of the plurality of aerosol particles comprises performing a lung mapping.

19. The method of claim 17, wherein the aerosol dispersion transit times correspond to differences in lung resistance and compliance between inhalation and exhalation of a plurality of pathways in the lung.

20. The method of claim 17, wherein the machine learning model is trained using at least one of k-nearest neighbors, neural networks, hidden Markov approaches, naïve Bayes, decision trees, ensemble methods, support vector machines, other Bayesian approaches, regression-based approaches, clustering approaches, dimensionality reduction approaches, Markowitz-based approaches, recurrent approaches, reinforcement learning, cross-validation and stochastic gradient descent, as well as combinations thereof.

* * * * *